United States Patent [19]
Mitsuhashi

[11] Patent Number: 5,976,797
[45] Date of Patent: *Nov. 2, 1999

[54] METHOD FOR QUANTIFYING TOTAL MRNA WITH POLY(A)-COMPLEMENTARY OLIGONUCLEOTIDE-IMMOBILIZED MICROTITER PLATE

[75] Inventor: Masato Mitsuhashi, Irvine, Calif.

[73] Assignees: Hitachi Chemical Co., Ltd., Tokyo, Japan; Hitachi Chemical Research Center, Inc., Irvine, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/772,150

[22] Filed: Dec. 20, 1996

[51] Int. Cl.$^6$ ........................................ C12Q 1/68
[52] U.S. Cl. ........................ 435/6; 536/24.3; 536/25.32; 435/287.2; 435/287.7; 435/288.3; 435/288.4; 424/9.2; 424/181.1
[58] Field of Search ................... 435/6, 287.2, 287.7, 435/288.3, 288.4, 91.1, 270; 536/24.3–24.33, 26.5, 25.32; 424/9.2, 181.1; 436/94

[56] References Cited
PUBLICATIONS

Shroder et al. Biochemistry 29: 2368–2378, Sep. 1990.

*Primary Examiner*—Kenneth R. Horlick
*Assistant Examiner*—Janell Taylor
*Attorney, Agent, or Firm*—Knobbe, Martens, Olson & Bear, LLP

[57] ABSTRACT

A method for quantifying total mRNA in a biological sample containing RNA such as crude cell lysates containing cytosolic mRNA, which method comprises the steps of: (a) incubating the sample with an oligo-(dT)- or poly-U-immobilized microtiter plate; (b) washing non-hybridized components from the microtiter plate; (c) labeling the hybridized mRNA with a photometric nucleic-acid dye; (d) measuring the amount of label captured on the microtiter plate; (e) heat-denaturing the labeled mRNA; (f) washing the denatured mRNA from the microtiter plate; and (g) measuring the amount of label remaining on the microtiter plate; and (h) correlating the amount of the measured label (captured label minus remaining label) with the quantity of total mRNA present in the sample, thereby easily measuring the total mRNA without the influence of rRNA or tRNA and without radioactive dyes, which method can be adapted to chemosensitivity tests.

12 Claims, 9 Drawing Sheets

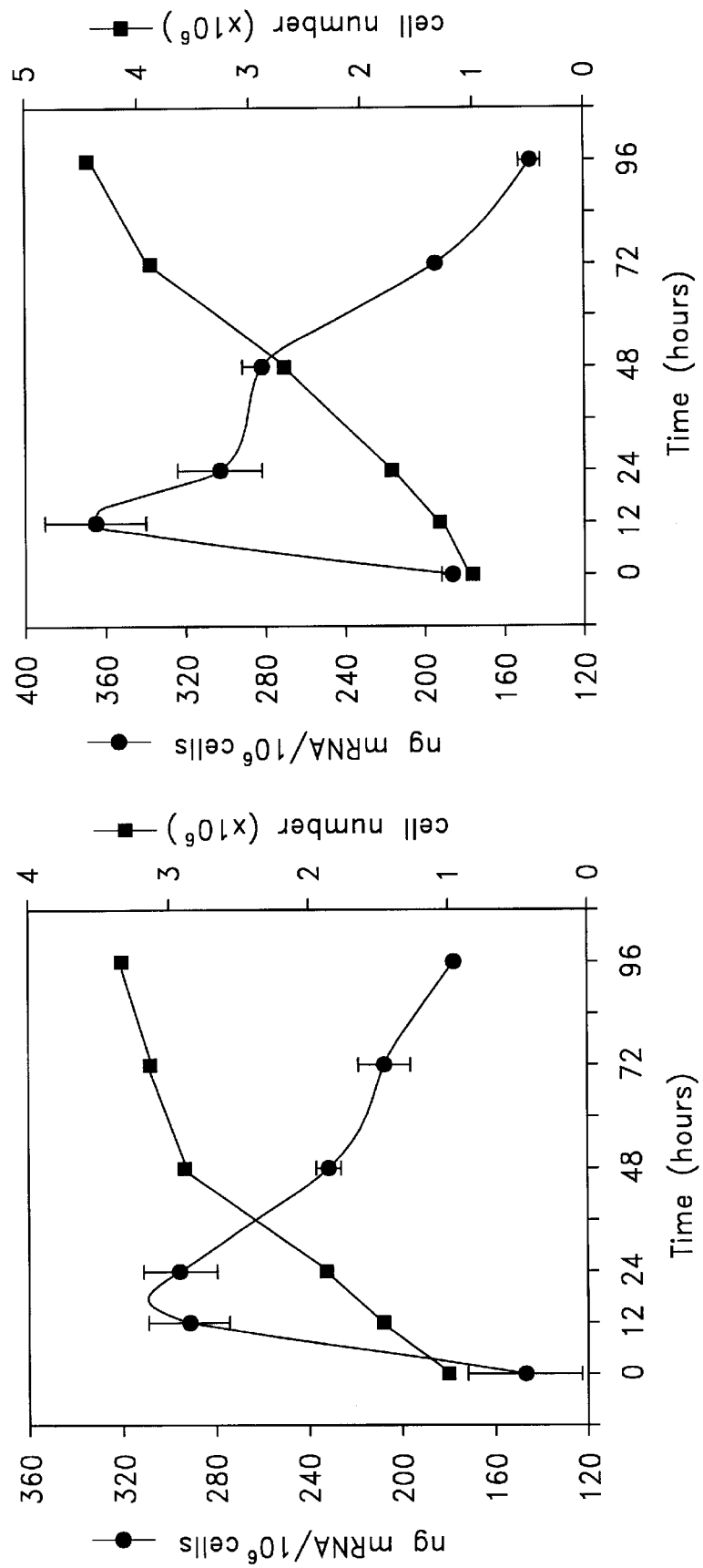

METHOD FOR QUANTIFYING TOTAL MRNA WITH POLY(A)-COMPLEMENTARY OLIGONUCLEOTIDE-IMMOBILIZED MICROTITER PLATE

BACKGROUND

1. Field of the Invention

This invention relates to a method for quantifying total mRNA in a biological sample such as crude cell lysates containing cytosolic RNA, and particularly to that for quantifying total mRNA by using a microtiter plate to which poly(A)-complementary oligonucleotides are immobilized, which method allows for a rapid, accurate, and nonradioactive quantification of total mRNA even when rRNA (ribosomal RNA) and tRNA (transfer RNA) are present in the sample. This invention also relates to a rapid chemosensitivity determination method using the total-mRNA measuring method.

2. Background of the Art

New gene sequences are discovered daily, and advanced molecular biological techniques are revolutionizing clinical practice in genetic disorders, oncology, infectious diseases, etc. Although the current major focus is set on use of DNA to identify disease genes, genetic mutations, translocations, or foreign genes as infectious agents, the analysis of specific mRNA also attracts clinical scientists who may wish to quantify specific gene expression in certain tissues and cells during the course of disease, both before and after various treatments.

Technologies are available for the analysis of mRNA, e.g., Northern blotting (Sambrooke et al., Molecular cloning, a laboratory manual, 2nd ed., Cold Spring Harbor, N.Y., Cold Spring Harbor Laboratory Press, 1989:7.28–7.52) and reverse transcription followed by polymerase chain reaction (RT-PCR: reverse transcription-polymerase chain reaction) (Kawasaki et al., Erlich HA, ed. PCR technology, New York, Stockton, 1989:89–97), and in each assay, positive signals can be quantified by various techniques. However, the comparison of positive signals among different clinical specimens is still quite difficult, given the lack of normalization procedures. For example, if specific mRNA expression in cancers is compared among different patients, such signals can be expressed in terms of wet weight, protein concentration, DNA content, RNA content, etc. The most common practice in Northern blotting is to apply the same amounts of RNA and confirm that ribosomal RNA (rRNA) signals of the same intensity are observed on the same filters (Okamoto et al., Biochem Biophys Res Commun 1993; 197:878–85). However, because the mRNA content accounts for less than 5% of total RNA or rRNA, the same amount of measured total RNA or rRNA does not indicate that the amount of applied mRNA is equal among tested samples.

Alternatively, one can compare specific signals with the expression of other, known housekeeping genes, e.g., β-actin (Ponte et al., Mol Cell Biol 1983; 3:1783–91) and glyceraldehyde-3-phosphate dehydrogenase (Tso et al., Nucleic Acids Res 1985; 13:2485–502). However, the expression of these genes is also known to vary substantially under certain conditions. The most practical solution is to purify mRNA and use the same amount of mRNA for Northern blots or for RT-PCR, even though purification of the mRNA requires additional time-consuming steps.

Other attempts have been made to quantify the amount of total mRNA in test samples. In a classical approach, poly (A)+ mRNA is purified from test samples and the final amount of purified mRNA is determined by measuring $A_{260}$; however, this method requires a relatively large amount of starting material and multiple time-consuming steps. Johnson, et al. (Johnson et al., Cell 1974; 1:95–100 and Johnson et al., J Cell Biol 1976; 71:933–8), in a series of studies, chase-labeled mRNA with radioactive mononucleotides and determined the radioactivity of the purified RNA or mRNA. However, this method requires radioactive materials and chase-labeling mRNA, thereby providing non-absolute amount of mRNA. In flow cytometry, both DNA and RNA contents from acridine orange-stained cells were simultaneously determined by two-color analysis: green emission for DNA and red emission for RNA (Traganos et al., Cytometry 1982; 2:212–8 and Hadjlssotiriou et al., Br J Urol 1985; 57:668–75). However, mRNA cannot be determined by this method, since the dyes stain not only mRNA but also rRNA and tRNA. Although Harley (Harley CB, Gene Anal Tech 1987; 4:17–22) reported a quantitative method of measuring total amounts of mRNA by hybridizing radiolabeled oligo-(dT) or RNA on nitrocellulose membranes, this method required radioactive probes and a lengthy process such as probe hybridization, washing, and detection). Further, the assay is semiquantitative; it is uncertain whether the applied RNA samples are entirely immobilized on nitrocellulose membranes and available for hybridization to each probe.

Previously, we introduced a unique research system involving microtiter plates to which oligonucleotides containing oligo-(dT) sequences had been immobilized covalently (GenePlate™: Mitsuhashi et al., Nature 1992; 357:519–20). Furthermore, we also reported that DNA and RNA in solution (Ogura et al., BioTechniques 1994; 18:231–2), and oligonucleotides immobilized on a microtiter plate (Ogura et al., BioTechniques 1994; 18:1032–4) could be quantified by adding the fluorescent indicator dye YOYO-1™ (Glazer et al., Nature 1992; 359:859–61). However, heretofore, oligonucleotides have never been quantified with an indicator such as YOYO-1™ while being hybridized with oligonucleotides immobilized on a microtiter plate, because specificity and sensitivity of indicators were believed uncertain. In addition, it was difficult to separate signals of mRNA from those of rRNA and tRNA, leading to overestimation of total mRNA.

Biological significance of total mRNA has been reported: The amount of total mRNA in rapidly growing cells was significantly higher than that of resting cells (Johnson et al., Cell 1974; 1:95–100). However, measuring total mRNA has not been applied to medical or diagnostic use such as a chemosensitivity test in a practical manner, because rapid and sensitive measuring methods are not available.

To select the most appropriate anticancer drugs and their optimum doses, various chemosensitivity tests have recently become available, which include the method of identifying dead or dying cells by measuring increased cellular permeability (Ross et al., Cancer Res 1989; 49:3776–3782), the measurement of DNA synthesis using $^3$H-thymidine incorporation (Kern et al., Cancer Res 1985; 45:5346–5441), the measurement of cellular metabolic activities using MTT (3-(4,5-dimethylthiazol-2-yl)-2,5-diphenyltetrazolium bromide) (Mosmann et al., J Immuno Methods 1983; 65:55–63), AlomarBlue (Fields et al., American Biotechnology Laboratory, March 1993 and de Fries et al., J. Clin Lab Anal 1995; 9:89–95), etc. However, these assays require cell culture for at least a few days to detect the cytotoxic effect of anticancer drugs, although some cancer cells are extremely difficult to maintain in culture. Furthermore, because cellular phenotype may change significantly during culture conditions, the results of long culture may not correspond to the results in vivo (Bellamy et al., *Drugs* 1992; 44:690–708).

SUMMARY OF THE INVENTION

The present invention has exploited a rapid and accurate total mRNA measuring method and rapid chemosensitivity methods. An objective of the present invention is to provide a method for rapidly and accurately quantifying total mRNA.

Namely, one important aspect of the present invention is a method for quantifying total mRNA in a biological sample containing RNA, comprising the steps of: (a) incubating said sample with a microtiter plate to which oligonucleotides having nucleotide sequences complementary to the mRNA poly(A) tail (such as oligo-(dT) and poly-U) are immobilized covalently, to hybridize mRNA with said oligonucleotides at said nucleotide sequences; (b) washing non-hybridized components from said microtiter plate; (c) labeling with a photometric nucleic-acid dye mRNA hybridized with said oligonucleotides in step (a); .(d) measuring the amount of label captured on said microtiter plate; and (e) correlating the amount of the measured label with the quantity of total mRNA present in said sample. In the above, the method preferably further comprises, between step (d) and step (e), the steps of: (i) heat-denaturing said mRNA labeled in step (c); (ii) washing said denatured mRNA from said microtiter plate; and (iii) measuring the amount of label remaining on said microtiter plate; wherein, in step (e), the amount of the measured label is the amount of the captured label in step (d) minus the amount of the remaining label in step (iii). By using poly(A)-complementary oligonucleotide-immobilized microtiter plates to capture total mRNA and by using sensitive nucleic-acid dyes, surprisingly, the total mRNA can be easily and accurately measured without influence of rRNA or tRNA and without radioactive dyes. The above method takes less than 90 minutes from whole cells to the final results and requires no radioactive materials. In the above, the dye is preferably a fluorescent dye selected from the group consisting of 1,1'-(4,4,7,7-tetramethyl-4,7-diazaundecamethylene)-bis-4-[3-methyl-2,3-dihydro-(benzo-1,3-oxazole)-2-methylidene]-quinoliumetraiodide (Yoyo-1), 1,1'-(4,4,7,7-tetramethyl-4,7-diazaundecamethylene)-bis-4-[3-methyl-2,3-dihydro-(benzo-1,3-thiazole)-2-methylidene]-quinoliumetraiodide (TOTO-1™), 1,1 ' -(4,4,7,7-tetramethyl-4,7-diazaundecamethylene)-bis-4- [3-methyl-2,3-dihydro-(benzo- 1,3-thiazole)-2-propenylidene]-quinoliumetraiodide (TOTO-3™).

Further, in the method, said sample is preferably a crude cell lysate containing cytosolic mRNA. Once crude cell lysates are applied to the plate, poly(A)+ mRNA is captured on the plate by the poly(A)-complementary sequences of the immobilized oligonucleotide without previous preparation of mRNA. In addition, in the aforesaid method, the length of said poly(A)-complementary sequences in said oligonucleotides is preferably at least 15 bases, and, in the step of hybridization, RNase inhibitor VRC (vanadyl-ribonucleoside complex) is preferably added to said sample.

Because of its simplicity, rapidity, and the easy manipulation of microtiter plates, the method is useful not only in basic molecular biology but also in clinical diagnostics to analyze cellular activity and degrees of malignancy. Another object of the present invention is to provide a method for determining cytotoxic effects of a compound by using the aforesaid quantifying method, comprising the steps of: (a) adding said compound to sample cells to allow said compound to act on said sample cells for a predetermined period of time; (b) measuring the quantity of total mRNA present in said sample cells by the aforesaid quantifying method; and (c) correlating the quantity of the total mRNA with the cytotoxic effects of said compound. In order to develop a rapid chemosensitivity test, the total amount of poly(A)+ mRNA is measured because mRNA production is an earlier event than protein synthesis. In fact, the levels of total mRNA in cultured leukemia cells were rapidly changed by serum stimulation/deprivation (Miura et al., *Clin. Chem.* 1996; 42:11, 1758–1764). By measuring the amount of total cytosolic poly(A)+ mRNA, either cytocidal or cytostatic chemosensitivity can be detected at a much earlier stage than by conventional MTT assay. This system is suitable for determining cytotoxic effects of anticancer drugs. The preferable aspects of the aforesaid quantifying method can be applied to this aspect.

Still another object of the present invention is to provide a method for determining the quantity of a particular mRNA in a biological sample containing RNA by using the aforesaid quantifying method, comprising the steps of: (a) measuring the quantity of said particular mRNA; (b) measuring the quantity of total mRNA present in said sample by the aforesaid quantifying method; and (c) correlating the quantity of said particular mRNA with the quantity of the total mRNA. According to this method, it is possible to accurately evaluate the quantity of a particular mRNA based on the quantity of total mRNA, not based on a certain number of cells, eliminating deviation in the quantity of total mRNA in various cells. The preferable aspects of the aforesaid quantifying method can be applied to this aspect.

BRIEF DESCRIPTION OF THE FIGURES

FIG. 1 is a graph showing poly(A)+ mRNA hybridization on an oligo-(dT)-immobilized microtiter plate, wherein

FIG. 6 is a graph showing the relationship between mRNA production and time (hours) and between the number of cells and time (hours), i.e., the effects of serum stimulation on cytosolic mRNA, wherein the undifferentiated U937 cell line is used in FIG. 6A, and the undifferentiated HL-60 cell line is used in FIG. 6B.

DETAILED DESCRIPTION OF THE PREFERRED EMBODIMENTS

Characteristics of mRNA Assay

Figures 1A, 1B, 1C:
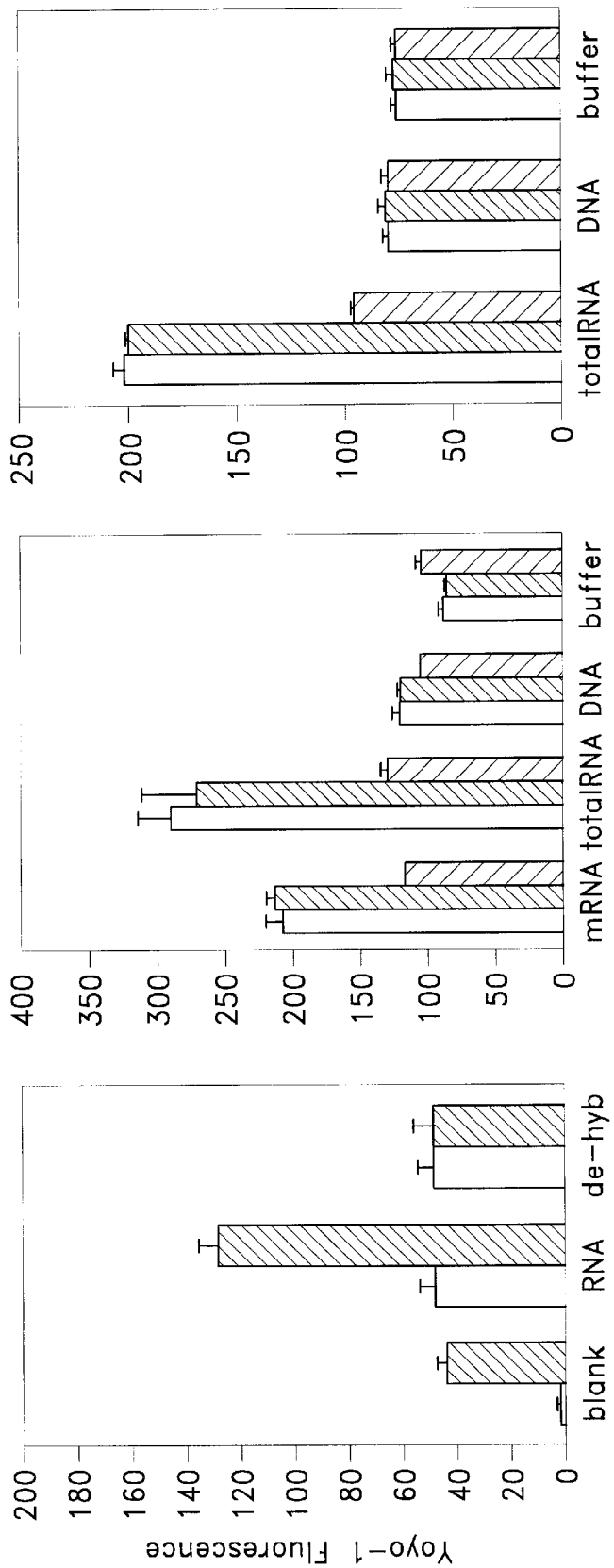
FIG. 1A shows reversibility of the oligo-(dT)-immobilized microtiter plate and of an oligonucleotide-free control plate.
FIG. 1B shows poly(A) specificity when first incubated with a hybridization buffer, poly-(dA) oligonucleotides, or poly-(dT) oligonucleotides.
FIG. 1C shows nuclease specificity when incubated with a buffer alone, DNase, or RNase.

The rapid and nonradioactive method of the present invention is suitable for measuring the amount of cytosolic mRNA from crude cell lysates without purifying mRNA. The mRNA assay using a poly(A)-complementary oligonucleotide-immobilized microtiter plate is specific for poly(A)+ sequences and sensitive to RNase, and hybridization is reversible (see Example 1 described later). Furthermore, the assay gives results comparable with those by conventional Northern blotting and absorbance determination at 260 nm (see Example 2 described later). These characteristics clearly satisfy the criteria for the measurement of poly(A)+ mRNA.

RNA could bind to a plastic plate itself irreversibly if other oligonucleotides have not been previously immobilized to the plate. Although such nonspecific binding of RNA to the plate can be eliminated by immobilization of oligonucleotides, signals of indicators such as YOYO-1™ are measured preferably before and after elution with hot water to determine the actual fraction of signals that are due to reversible hybridization. By subtracting postelution signals from preelution signals, potential well-to-well variation can be minimized.

The mRNA assay using a poly(A)-complementary oligonucleotide-immobilized microtiter plate unexpectedly allows for eliminating influence of the presence of tRNA and rRNA. Signals of mRNA increase in proportion to the amount of applied materials, while signals of tRNA and rRNA remain unchanged. The maximum amount of hybridized mRNA measured by the assay corresponds to the theoretical values, as described in Example 2 later. Conventional assays such as $A_{260}$ overestimates the mRNA content because measured values include tRNA and rRNA.

Because of the presence of RNases in cytoplasm, mRNA may be digested by RNases during hybridization procedures. In fact, in some cells, the amount of mRNA is substantially decreased if RNase inhibitors are not included in the cell lysis mixture. Therefore, for the best results, measuring the amount of cytosolic mRNA requires that RNase activity be eliminated. Fortunately, such RNase activities can be easily monitored by YOYO-1™, for example, because YOYO-1™ fluorescence decreases when RNA or RNA YOYO-1™ complex is digested by RNases. VRC is the most effective RNase inhibitor among others such as RNasin (Promega). In the presence of 10–20 mmol/L VRC in cell lysate, results of the measurement of cytosolic mRNA can effectively stay constant even after hybridization of 1 hour or more. In the present invention, therefore, VRC are preferably included in a lysis buffer.

About 1–5 μg of mRNA is obtained from $10^7$ cells (Sambrook et al., Cold Spring Harbor Laboratory Press, 1989:7.28–7.52). According to the manual accompanying the FastTrack mRNA purification kit, a typical yield of mRNA from $10^8$ cells is 10–85 μg. The amount of cytosolic mRNA measured by the present invention (for example, ~250–300 ng per $10^6$ cells) is within that range.

The fraction of RNA in DNA or in total nucleic acids is known to vary among different cells and provides an indicator for cell growth (Traganos et al., *Cytometry* 1982; 2:212–8) and malignancy (Hadjlssotiriou et al., *Br J Urol* 1985; 57:668–75). The total mRNA content is also significantly higher in rapidly growing cells than in resting cells (Johnson et al., *Cell* 1974; 1:95–100 and Johnson et al., J Cell Biol 1976; 71:933–8). The present invention shows similar results; i.e., the amount of total cytosolic mRNA measured by the present method is much higher in undifferentiated cells than in differentiated cells (see Example 3 described later). Furthermore, by removing differentiated cells from the culture plates and using the microscope to compare their size with that of undifferentiated cells, it is found that the differentiated cells are slightly larger than undifferentiated cells, i.e., the difference in mRNA content could not be explained by the changes in cell size.

Differentiated cells are adherent, whereas undifferentiated cells float unattached. Such differences in cellular characteristics may account for the difference in mRNA content. However, in recent studies (manuscript in preparation), another adherent cell line, e.g., CaR-1 human colon cancer cells, expressed ~300–350 ng of cytoplasmic mRNA per $10^6$ cells, despite their nonadherent nature (manuscript in preparation). Therefore, the changes in mRNA content may be more correlated with cellular differentiation than with cellular phenotype, and the abundance of mRNA in undifferentiated cells may be related to increased metabolic activities, e.g., of cancer cells.

Because mRNA synthesis occurs earlier than protein synthesis, the changes in mRNA content are observed very quickly after serum stimulation of cultured cells (Johnson et al., *Cell* 1974; 1:95–100). Interestingly, in the present invention, the response of mRNA to growth stimuli is more sensitive in undifferentiated cells than in differentiated cells (Example 3 described later). Furthermore, the amounts of mRNA in undifferentiated cells decrease rapidly by deprivation of serum (FCS), whereas the mRNA content remains stable in differentiated cells. Hyperresponsiveness to serum deprivation may be related to the cellular differentiation status, not to the cell's adherent/floating characteristics.

The method of the present invention takes 90 minutes or less from whole cells to the final results and requires no radioactive materials. Because of its simplicity, rapidity, and the easy manipulation of microtiter plates, the method is useful not only in basic molecular biology but also in future clinical diagnostics to analyze cellular activity and degree of malignancy. By using as a denominator a total mRNA value obtained by the total mRNA assay of the present invention, it is possible to more appropriately evaluate production of a particular mRNA than by using as denominator the number of cells.

Cytotoxicity Assay

Since mRNA synthesis is an earlier event than protein synthesis followed by cellular metabolic activities or cellular proliferation, the mRNA assay of the present invention is able to detect cytotoxicity earlier than any other conventional assays (Ross et al., *Cancer Res* 1989; 49:3776–3782, Kern et al., *Cancer Res* 1985; 45:5346–5441, Mosmann et al., *J. Immuno Methods* 1983; 65:55–63, Fields et al., *American Biotechnology Laboratory*, March 1993, and de Fries et al., *J Clin Lab Anal* 1995; 9:89–95). Some specific mRNA may also be discovered in future, which could detect chemosensitivity at a much earlier stage than can total mRNA. Although the amount of each specific mRNA is much less than that of total mRNA, it is possible to measure it using the mRNA assay of the present invention. However, because different mRNA may be responsible for the action of each drug in different cells, multiple specific mRNA tests are required for each drug and each cancer, whereas a total mRNA assay is applicable to any circumstances as a single universal chemosensitivity test.

The early detection of chemosensitivity provides not only rapid determination of appropriate drugs for therapy, but also more feasible and reliable data by eliminating the necessity of cell culture. Furthermore, mRNA assay is responsible for both cytocidal and cytostatic drug sensitivity, the assay may be suitable for initial screening for drug activities. Unlike $^3$H-thymidine, MTT, AlomarBlue assays, where isolated cells should first be incubated with reporter molecules in vitro for a certain length of time, the amount of cellular mRNA can be quantified at the time when cells cancer cells in, biopsy and tissue specimens are surgically removed before and after chemotherapy, and in vivo response of cancer cells to each drug will be monitored, although an additional hardship exists in isolating cancer cells from solid tumors. Because a total mRNA assay provides various advantages over existing technologies as described above, the assay is suitable as the subject of clinical studies to prove whether the results obtained in cultured cells in the present invention are applicable to clinically isolated cells with relevant drugs and their combinations. Chemosensitivity tests can be performed on any compounds associated with cell death and/or cell growth. Such compounds include anticancer drugs such as cisplatin, vinblastine, mitomycin, etc. but are not limited thereto.

Poly(A)-Complementary Oligonucleotides

In the present invention, the immobilized oligonucleotides include nucleotide sequences complementary to the mRNA polyadenylic acid tail (poly(A) tail) or capable of hybridizing mRNA at the poly(A) tail. Such complementary sequences includes oligo-(dT) as well as poly-U. Oligonucleotides containing oligo-(dT) sequences are suitably used for an oligonucleotide-immobilized microtiter plate. The length of oligo-(dT) or poly-U sequences is preferably at least 15 mers, normally 15–40 mers. If the sequence is shorter than that, the oligo-(dT) or poly-U sequence cannot securely capture poly(A) tails of mRNA. Technologically no upper limit is imposed on length, and nucleotides having 100 mers can be used. The oligonucleotides can include nucleotide sequences other than oligo-(dT) or poly-U such as sequences of restriction sites (e.g., EcoRI, NotI, etc.) and sequences of promoters such as T7 promoter. Nucleotide sequences can be selected as necessary. Polynucleotide sequences of various lengths, including 30 to 100-mers, can be readily synthesized using techniques known to those of ordinary skill in the art.

Microtiter Plate and Immobilization Methods

Nucleotides having poly(A)-complementary sequences are immobilized on a microtiter plate. The term "microtiter plate" means insoluble disks in a desired shape, typically plastic (or glass) microtiter plates. Various methods of immobilizing polynucleotides to the insoluble support are available. However, the covalent binding method is most preferred. The polynucleotides are immobilized to microtiter plates which exhibit functional groups, such as carboxyl residues, amine residues, or hydroxyl residues on the surface thereof. Preferably, plastic plates which express carboxyl residues or primary amine residues on the surface are used.

Examples of plastic plates containing carboxyl residues and primary amine residues on the surface are the "Sumilon" microplates MS-3796F and MS-3696F, available from Sumitomo Bakelite.

In a preferred procedure for immobilization of the polynucleotide to a microtiter plate exhibiting a functional group, the 5'-terminal end of the polynucleotide is covalently linked to the functional group by well-known methods including the maleimide method and carbodiimide method.

The maleimide method involves the reaction between a substance containing a maleimide group and another material containing a sulfhydryl residue (SH). In order to attach the 5' end of a polynucleotide to an immobilized support using the maleimide method, the 5' end of the polynucleotide is reacted with a maleimide compound. A suitable maleimide compound is sulfosuccinimidyl-4-(N-maleimidomethyl) cyclohexane-1-carboxylate (sulfo-SMCC). The SH residue is provided on the support by a reaction between a support having an amine residue and succinimidyl-S-acetylthioacetate (SATA), followed by deacetylation using hydroxylamine ($NH_2OH$). (Sulfo-SMCC and SATA are readily available from a variety of commercial sources, including the Pierce Company.) The resulting SH group on the support can then react with the maleimide group on the 5' end of the polynucleotide to form a polynucleotide-immobilized support. In order to assure that the polynucleotides are immobilized at their 5' ends, the amine groups on the purine bases can be protected by pairing the polynucleotide to a complementary polynucleotide prior to immobilization. After immobilization, the complementary polynucleotide can be removed through denaturation, such as through heating.

The carbodiimide method involves a reaction between a carbodiimide compound with an amine residue and a material containing a carboxyl residue. An example of a carbodiimide compound is 1-ethyl-3-(3-dimethyl-aminopropyl) carbodiimide hydrochloride (hereafter called EDC). In order to use EDC in the carbodiimide method, EDC must first be activated to transform to an EDC compound containing an amine residue. This can be done by reaction with N-hydroxysulfosuccinimide (hereafter called Sulfo-NHS). Both EDC and Sulfo-NHS are available from well known commercial sources, including the Pierce Company. In the practice of a preferred carbodiimide method for attaching polynucleotides to a support, a support having a carboxyl residue attached is used. EDC is activated by reaction with Sulfo-NHS. This activated EDC is reacted with support-containing surface- bound carboxyl residues. This can then be reacted with polynucleotides having an amine residue at their 5'-terminal ends, resulting in a polynucleotide-immobilized support.

Non-specific binding of activated amine or carboxyl residues on insoluble supports can be effectively reduced or eliminated by treating plates to which polynucleotides have been immobilized with a primary amine compound, preferably glycine.

As a result, approximately 0.5–2 pmol (typically 1–1.5 pmol) of oligonucleotide are normally immobilized at the 5' end on the surface of a microtiter plate.

Nucleic Acid Dye

There are a variety of commercially-available, photometric nucleic-acid dyes. These include ethidium bromide, in addition to newer dyes made from the general groups of benzoxazolium-4-pyridinium, benzothiazolium-4-pyridinium, benzoxazolium-4-quinolinium (e.g. YOYO-1™) and benzothiazolium-4-quinolinium (e.g. TOTO-1™, TOTO-3™). However, in view of sensitivity and linearity, fluorescent dyes selected from the group consisting of YOYO-1™ (1,1'-(4,4,7,7-tetramethyl-4,7-diazaundecamethylene)-bis-4-[3-methyl-2,3-dihydro-(benzo- 1,3-oxazole)-2-methylidene]-quinoliumetraiodide), TOTO-1™ (1,1 '-(4,4,7,7-tetramethyl-4,7-diazaundecamethylene)-bis-4-[3-methyl-2,3-dihydro-(benzo-1,3-thiazole)-2-methylidene]-quinoliumetraiodide), Toto-3 (1,1'-(4,4,7,7-tetramethyl-4,7-diazaundecamethylene)-bis-4-[3-methyl-2,3-dihydro-(benzo-1,3-thiazole)-2-propenylidene]-quinoliumetraiodide), and are preferred. YOYO-1™ has an excitation wavelength of 485 nm, after excitation YOYO-1™ emits photons at 530 nm. Both of these wavelengths are in the visible light spectrum. Other dyes can also be contemplated, such as benzoxazolium-4-pyridinium, benzothiazolium-4-pyridinium, benzoxazolium-4-quinolinium, and benzothiazolium-4-quinolinium fluorescent dyes that show advantageous spectrographic sensitivity for the analysis of nucleic acid sequences. These dyes have excitation wavelengths from the low 400 nm range and emission wavelengths up to the high 600 nm range when bound to a nucleic acid sequence. Such dyes are commercially available from companies such as Molecular Probes, Inc. As a photometric dye, phosphorescence dyes and luminescence dyes can be used in place of fluorescence dyes. Incidentally, YOYO-1™ can function as a phosphorescence dye.

Particular mRNA Sequence

In the present invention, it is possible to calculate the ratio of the quantity of a particular mRNA to the quantity of total mRNA, which allows for determining biological significance of the quantity of the particular mRNA. The quantity of total mRNA measured by the present invention represents absolute quantity of total mRNA which is neither a relative evaluation nor includes rRNA or tRNA. Various methods for quantifying a particular mRNA are available such as Northern blotting techniques and microtiter-plate hybridization techniques.

<EXAMPLE: MEASURING TOTAL mRNA>

Materials

We obtained from the respective suppliers human Jurkat, Molt-4, U937, and HL-60 cells (American Type Culture Collection, Rockville, Md.); MICROFAST TRACK™ 228 Kit (mRNA purification kit using oligo-(dT) cellulose, (Invitrogen, San Diego, Calif.); cell culture media, fetal calf serum, (FCS: fatal calf serum), phosphate-buffered saline (PBS: phosphate-buffered saline), rabbit globin mRNA, and vanadyl-ribonucleoside complex (VRC: vanadyl-ribonucleoside complex; Gibco-BRL, Baithersburg, Md.); Isolymph (Gallard-Schlesinger, Carle Place, N.Y.); calf thymus DNA (Clontech, Palo Alto, Calif.); DNase (Boehringer Mannheim, Indianapolis, Ind.); RNase (Stratagene, La Jolla, Calif.); and GENEPLATE™ (oligonucleotide-immobilized microplate,(Hitachi Chemical Research Center, Irvine Calif. and Hitachi Chemical Co., Ibaraki, Japan). All other chemicals were purchased from Sigma Chemical Co. (St. Louis, Mis.). Oligonucleotides were synthesized by a synthesizer (Applied Biosystems, San Jose, Calif.), according to the manufacturer's protocol.

Cell culture

Human Jurkat and Molt-4 cells were grown in RPMI 1640 containing 100 U/mL penicillin, 100 µg/mL streptomycin, and 100 mL/L FCS at 37° C. in $CO_2$:air, 5:95 (by vol). U937 and HL-60 cells were grown in RPMI 1640 containing 100 mL/L FCS and were treated with 160 nmol/L phorbol 12-myristate 13-acetate (PMA: phrbol 12-myristate 13-acetate) for one to three days to induce differentiation, as previously described (Mitsuhashi et al., *J Biol Chem* 1989; 264:18356–62). In the present study, only adherent cells were used as differentiated cells. Each cell line was subcultured two to three times a week, and viability was always >90%, as assessed by the exclusion of trypan blue. The number of cells was determined with a hemocytometer.

Preparation of cell suspension

Blood was obtained from healthy human donors after they gave their informed consent; procedures were in accordance wit the Helsinki Declaration of 1975, as revised in 1983. Heparinized blood taken from healthy adults was diluted threefold with PBS and was layered over IsoLymph. After centrifugation at 400 g for 30 minutes at room temperature, the interphase containing the mononuclear leukocytes was removed and washed with PBS three times. Undifferentiated cultured cells were also washed with PBS two to three times. For removal from the tissue culture plates, the differentiated cells were treated with a solution of 2.5 mg/L trypsin and 1 mmol/L EDTA in isotonic saline for five minutes and then were washed with PBS.

Fluorometric measurement of mRNA

Cells were resuspended in 200 µL of diethylpyrocarbonate (DEPC)-treated lysis buffer (10 mmol/L Tris, pH 7.5, 1 mmol/L EDTA, 0.5 mol/L NaCl, 5 mL/L NP-40 detergent, and 20 mmol/L VRC) for five minutes on ice and then centrifuged at 15 000 g at 4° C. for five minutes. We then applied to either the GENEPLATE™ (oligonucleotide-immobilized or to microplate) control plates (without any oligonucleotides) 50 µL each of the supernatant solutions and treated them all identically to the treatment for the GENEPLATE™ (oligonucleotide-immobilized microplate). After a 1-h incubation at room temperature, unbound materials were removed by aspiration, and the plates were washed twice with low-salt buffer (10 mmol/L Tris, pH 7.6, 1 mmol/L EDTA, 0.1 mol/L NaCl). We added to each well 50 µL of YOYO-1™ (final dilution 1:1000) and measured the fluorescence intensity of each well with a fluorescent plate reader (CYTOFLUOR™ 228 2300: fluorescent plate reader; Millipore, Bedford, MAP) with excitation and emission wavelengths of 485 nm (bandwidth 20 nm) and 530 nm (bandwidth 25 nm), respectively. After measuring the YOYO-1™ fluorescence, we washed each well twice with 50 µL of boiled DEPC-water to elute the mRNA, and again measured the YOYO-1™ fluorescence. The YOYO-1™ fluorescence of each well was determined by subtracting the second YOYO-1™ fluorescence from the first.

Northern hybridization

Various amounts of rabbit globin mRNA were loaded onto 1% agarose gel containing 67 mL/L formaldehyde in 1× MOPS buffer (0.02 mol/L MOPS, 8 mmol/L sodium acetate, 1 mmol/L EDTA). After running the gel in 1× MOPS buffer at 100 V, the mRNA was transferred to a nylon membrane at a positive pressure of 2 kPa for 90 minutes (Posiblot; Stratagene) and then subjected to ultraviolet radiation-induced crosslinking (Crosslinker; Stratagene). The membrane was prehybridized in hybridization buffer—0.15 mol/L NaCl, 0.015 mol/L sodium citrate, pH 7.0, 20 mmol/L $NaH_2PO_4$, 70 mL/L sodium dodecyl sulfate (SDS: dodium dodecyl sulfate), 10× Denhardt solution, 100 g/L dextran sulfate, 100 µg/mL denatured herring sperm DNA—at 34° C. for 2 h and then was hybridized with $^{32}P$-labeled oligo-(dT) for 48 h at 34° C., as previously described (Okamoto et al., *Biochem Biophys Res Commun* 1993; 197:878–85). Labeled probes were prepared with $t_4$ polynucleotice kinase with the use of 50 pmol of oligonucleotides and 100 µCi of γ-$^{32}P$-ATP (3000 kCi/mol). After the membranes were washed with washing solution (1× SSC, 10 mL/L SDS, 0.5 mol/L NaCl), they were exposed to x-ray film for 3 h.

EXAMPLE 1: mRNA Specificity

The cytosolic RNA derived from $5\times10^5$ human mononuclear leukocytes was first applied to either oligonucleotide-free control plates or the oligonucleotide-immobilized GENEPLATE™ (oligonucleotide-immobilized microplate) for hybridization. When YOYO-1™ was applied to the plates before hybridization, the YOYO-1™ fluorescence was significantly higher on the GENEPLATE™ (oligonucleotide-immobilized microplate) than on the control plates (FIG. 1A, blank). This confirmed our previous work (Ogura et al., *BioTechniques* 1994; 18:1032–4) on quantifying the amount of immobilized oligonucleotides by YOYO-1™. After RNA hybridization, YOYO-1™ signals increased in both places (FIG. 1A, RNA). However, after we added hot water to elute the mRNA and removed that mRNA by aspiration, YOYO-1™ fluorescence was decreased only on the plates of GENEPLATE™ (oligonucleotide-immobilized microplate), but not on the control plates (FIG. 1A, de-hyb).

Figure 3:
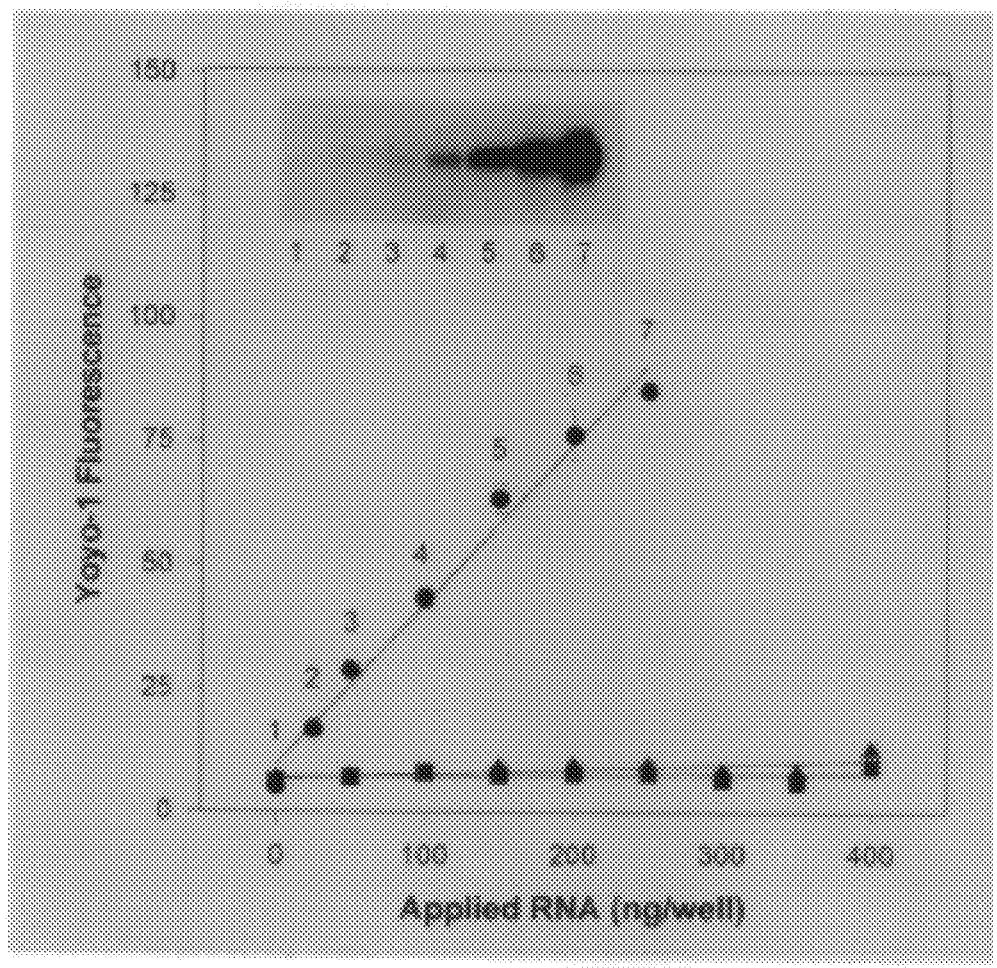
FIG. 3 is a graph showing the relationship between Yoyo-1 fluorescence and applied RNA (mRNA, tRNA, or rRNA), i.e., dose dependency of mRNA hybridization.

Furthermore, high YOYO-1™ signals were obtained for samples containing mRNA or for total RNA, but not for the buffer alone, DNA (FIG. 1B), or rRNA or transfer RNA (tRNA) (see FIG. 3). To analyze poly(A) sequence specificity of hybridized RNA, we first incubated the GENEPLATE™ (oligonucleotide-immobilized microplate) with either a hybridization buffer alone or 10 pmol of either 17-mer poly-(dA) or poly-(dT) oligonucleotides at room temperature for 1 h. After hybridization, the plates were washed with hybridization buffer twice to remove unbound oligonucleotides, then mixed with various test solutions as described above. As shown in FIG. 1B, significant YOYO-1™ signals were obtained from rabbit globin mRNA and total cytosolic RNA derived from human Jurkat cells, but remained at basal values when the GENEPLATE™ (oligonucleotide-immobilized microplate) had been incubated previously with poly-(dA), but not poly-(dT) (FIG. 1B).

We have previously shown that YOYO-1™ signals of DNA and RNA were significantly decreased after digestion with DNase and RNase, respectively (Glazer et al., *Nature* 1992; 359:859–61). Therefore, to further confirm whether YOYO-1™ signals on the GENEPLATE™ (oligonucleotide-immobilized microplate) were derived from either RNA or contaminating DNA, we treated the hybridized GenePlate with either DNase or RNase. As a result, high Yoyo-1 signals from total cytosolic RNA were diminished only after treatment with RNase, but not with DNase (FIG. 1C).

As shown in FIG. 1A (white bar), RNA could bind to the plastic plate irreversibly if oligonucleotides had not first been immobilized to the plates. Although such nonspecific binding of RNA to the plate was eliminated by immobilization of oligonucleotides, we measured YOYO-1™ fluorescence before and after elution with hot water to determine the actual fraction of YOYO-1™ fluorescence that was due to reversible hybridization. By subtracting postelution YOYO-1™ fluorescence from preelution YOYO-1™ fluorescence, potential well-to-well variation was minimized.

In the above, FIG. 1 shows Poly(A)+ mRNA hybridization on the GENEPLATE™ (oligonucleotide-immobilized microplate) reversibility (FIG. 1A); poly(A) specificity (FIG. 1B); and nuclease specificity (FIG. 1C). In FIG. 1A, cytosolic RNA derived from $5\times10^5$ human mononuclear leukocytes was suspended in hybridization buffer (10 mmol/L Tris, pH 7.5, 1 mmol/L EDTA, 0.5 mol/L NaCl, 10 mmol/L VRC), and applied to either the GENEPLATE™ (oligonucleotide-immobilized microplate) (□) or oligonucleotide-free control plates (□); all plates were treated identically. After a 1-h incubation at room temperature, unbound material was removed by aspiration and the plates were washed twice with low-salt buffer (10 mmol/L Tris, pH 7.6, 1 mmol/L EDTA, 0.1 mol/L NaCi). We added 50 μL of YOYO-1™ (final dilution 1:1000) to each well and measured the fluorescence intensity of each well with a fluorescent plate reader (CYTOFLUOR™ 228 2300: fluorescent plate reader) with excitation and emission wavelengths of 485 nm (bandwidth 20 nm) and 530 nm (bandwidth 25 nm), respectively. To test the reversibility of hybridization, we washed some wells twice with 50 μl/L of boiled DEPC water, then measured the fluorescence intensity as described above. (This experiment is reproduced many times during manufacturing of the GENEPLATE™ (oligonucleotide-immobilized microplate) as part of the quality-assurance protocols.) In FIG. 1B, to test poly(A) specificity, we first incubated the GenePlate with either a hybridization buffer (□), 10 pmol of 17-mar poly-(dA) (□), or 17-mar poly-(dT) oligonucleotides (□) at room temperature for 1 h. After hybridization, the GENEPLATE™ (oligonucleotide-immobilized microplate) was washed with hybridization buffer twice to remove unbound oligonucleotides, and then rabbit globin mRNA (150 ng), cytosolic total RNA derived from $5\times10^5$ human Jurkat cells (7.5 μg), calf thymus DNA (500 ng), and hybridization buffer alone were applied to each GENEPLATE™ (oligonucleotide-immobilized microplate) for hybridization. The Yoyo-1 fluorescence was then measured with the fluorescent plate reader. In FIG. 1C, cytosolic RNA derived from $5\times10^5$ human Molt-4 cells and 500 ng of calf thymus DNA was suspended in hybridization buffer, and then applied to the GENEPLATE™ (oligonucleotide-immobilized microplate) for hybridization. After a 1-h incubation at room temperature, unbound material was removed by aspiration, and each well was incubated with either buffer alone (□), DNase (20 U/mL) (□), or RNase (10 μg/mL) (□) at 37° C. for 30 minutes. The YOYO-1™ fluorescence was then measured. All data in FIGS. 1A, 1B, and 1C are the mean ±SE from triploste determinations.

EXAMPLE 2: Kinetics and Dose Dependency

Figure 2:
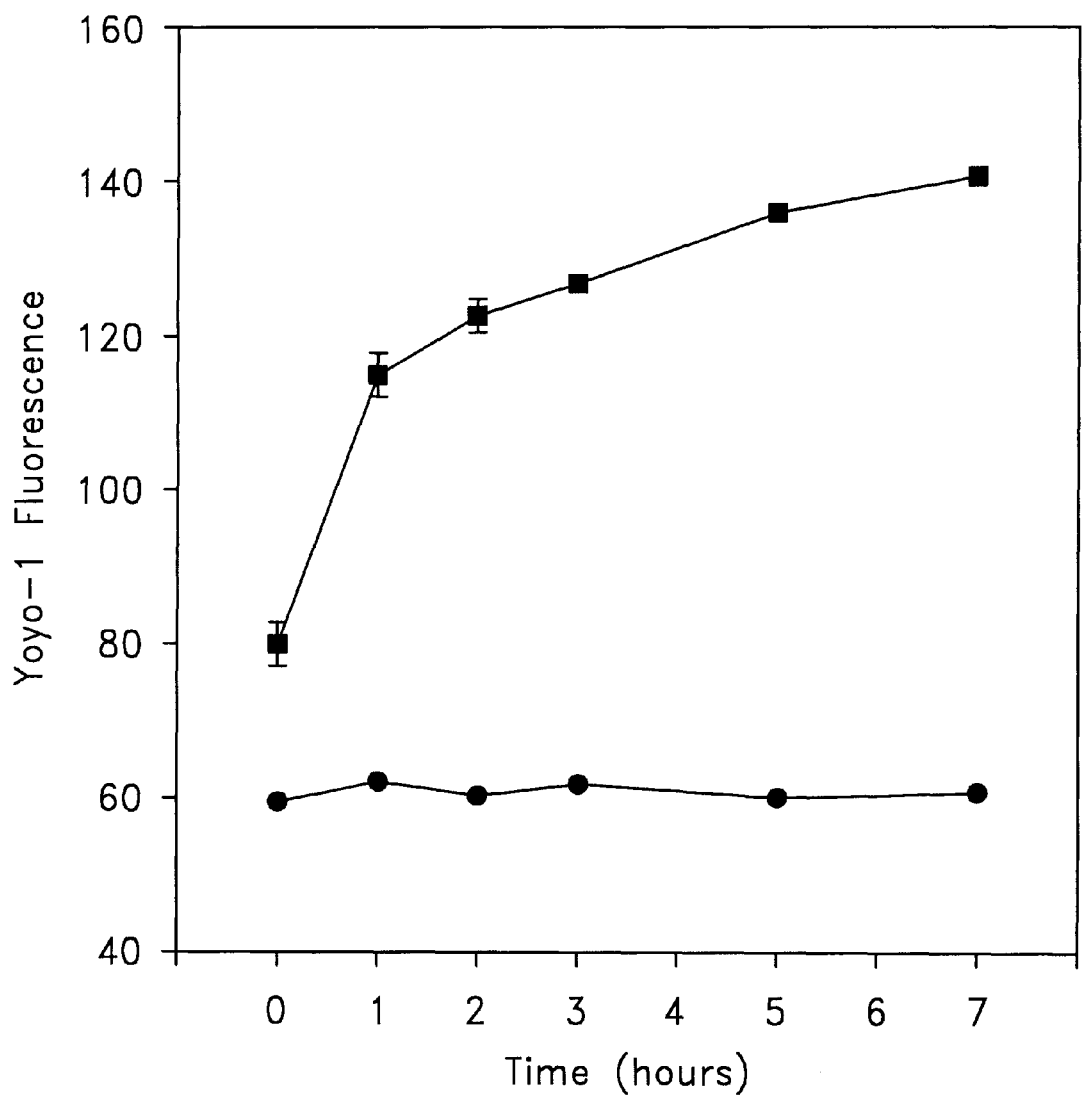
FIG. 2 is a graph showing the relationship between Yoyo-1 fluorescence and time (hours), i.e., kinetics of mRNA hybridization, when using the oligo-(dT)- immobilized microtiter plate and the oligonucleotide-free control plate.

Rabbit globin mRNA (250 μg) was applied to either control plates or the GENEPLATE™ (oligonucleotide-immobilized microplate) at room temperature for various lengths of time, after which the hybridized mRNA was quantified by Yoyo-1™. As shown in FIG. 2, YOYO-1™ fluorescence on the GENEPLATE™ (oligonucleotide-immobilized microplate) increased rapidly, reaching a plateau after 1 h, whereas the low Yoyo-1™ fluorescence on control plates remained unchanged. Similar kinetics were reproduced >10 times with various materials, including cytosolic RNA, cell lysates, and synthesized mRNA (data not shown).

YOYO-1™ fluorescence of hybridized rabbit globin mRNA was increased in proportion to the amount of applied materials up to 250 ng, whereas Yoyo-1™ signals of tRNA and rRNA remained unchanged (FIG. 3). Therefore, the amounts of hybridized mRNA can be quantified by comparing its fluorescence with that of known concentrations of hybridized mRNA. The linear range of hybridized mRNA on the GENEPLATE™ (oligonucleotide-immobilized microplate) was approximately 10–250 ng (FIG. 3) and reached a plateau at >250 ng of mRNA (data not shown). Because approximately 1 pmol of oligonucleotide was immobilized on the GENEPLATE™ (oligonucleotide-immobilized microplate) (Ogura et al., *BioTechniques* 1994; 18:1032–4), the maximum capacity of mRNA on the GENEPLATE™ (oligonucleotide-immobilized microplate) was approximately 300 ng, calculated from 1000 bases of mRNA, each with 300 Da of ribonucleotide. Therefore, the maximum amount of hybridized mRNA measured by our method corresponds to the theoretical values. We have also compared our YOYO-1™ method with two other available techniques. First, various amounts of rabbit globin mRNA were separated by agarose gel electrophoresis, and transferred to nylon membranes, followed by hybridization with $^{32}$P-labeled oligo-(dT) (Northern blotting). The YOYO-1™ method was comparable with the results of Northern blot analysis (FIG. 3, inset).

Figure 4:
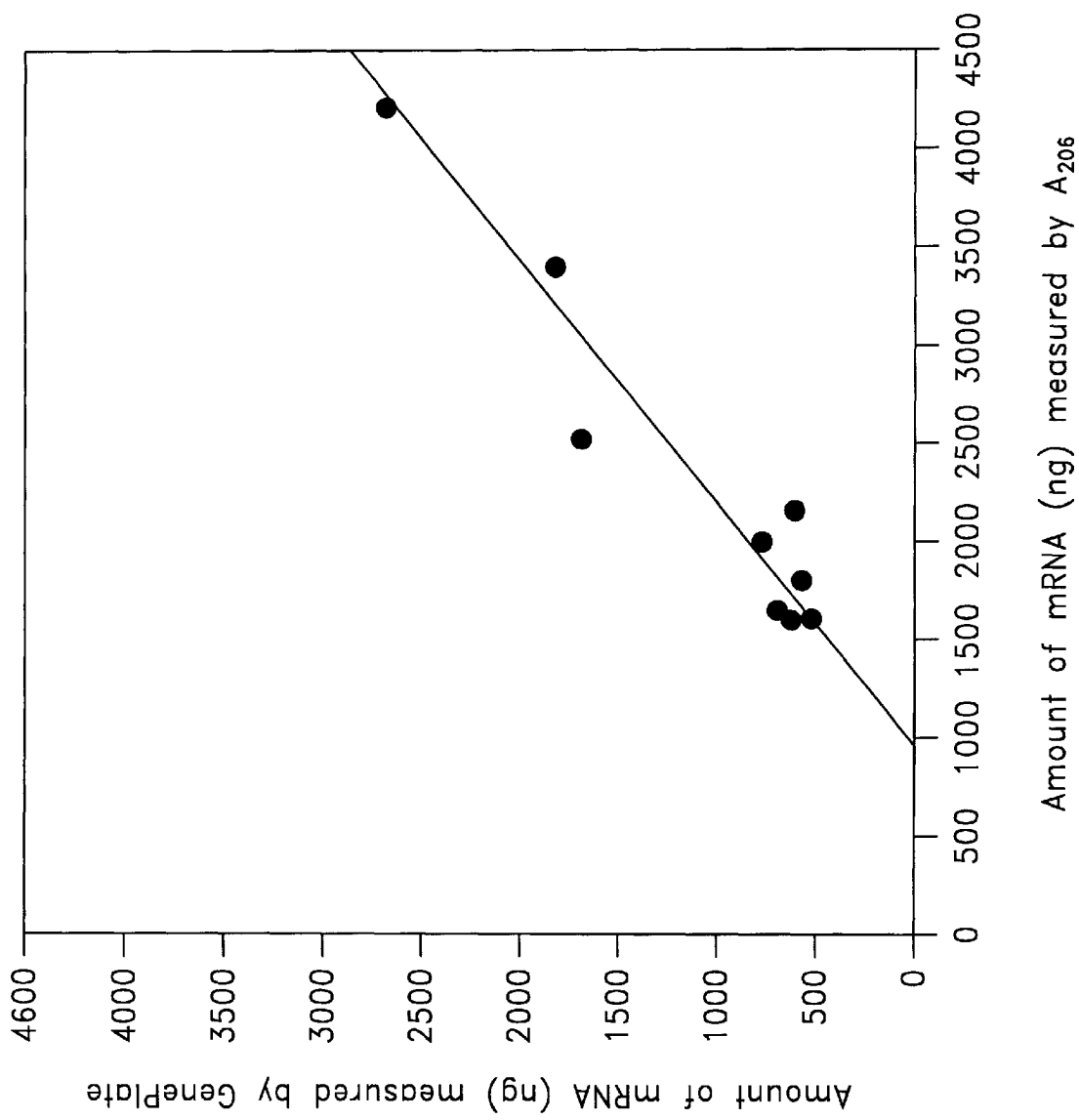
FIG. 4 is a graph showing the relationship between the amount of mRNA measured by the GenePlate and the amount of mRNA measured by $A_{260}$.

We also purified mRNA from U937 cells and various mouse tissues (kidney, liver, brain, heart) by a standard oligo-(dT) cellulose-based purification procedure (MicroFastTrack; Invitrogen) and measured the mRNA by both the GENEPLATE™ (oligonucleotide-immobilized microplate) assay and absorbance at 260 nm. The amount of mRNA on the GENEPLATE™ (oligonucleotide-immobilized microplate) was determined from the calibration curve for rabbit globin mRNA; in absorbance-based analysis, we used the formula 1.0 $A_{-260}$=40 μg of mRNA per milliliter. YOYO-1™ fluorescent on the GENEPLATE™ (oligonucleotide-immobilized microplate) and $A_{-260}$ were well correlated with each other (FIG. 4).

In the above, FIG. 2 shows kinetics of mRNA hybridization. Rabbit globin mRNA (250 ng) was applied to either the GENEPLATE™ (oligonucleotide-immobilized microplate) (■) or oligonucleotide-free control plates (●), all of which were treated identically. After incubation at room temperature for various times, YOYO-1™ fluorescence was measured with a fluorescence plate reader. All data are the mean ±SE from triplicate determinations. FIG. 3 shows dose Dependency of mRNA hybridization. Various concentrations of rabbit globin mRNA (●), tRNA (▲), and rRNA (■) in a total volume of 50 mL were applied to the GENEPLATE™ (oligonucleotide-immobilized microplate) for hybridization. The YOYO-1™ fluorescence was measured before and after elution as described in the text and FIG. 1. The fluorescence of hybridized RNA, minus that obtained after elution of each well, is expressed as the mean ±SE from triplicate determinations. The inset shows a typical autoradiogram (exposed for 30 min) of various concentrations of rabbit globin mRNA separated by agarose gel electrophoresis and subjected to Northern blot analysis on nylon membrane probed with $^{32}$P-labeled oligo-(dT) as described in the text. FIG. 4 shows a comparison of mRNA measured by the GENEPLATE™ (oligonucleotide-immobilized microplate) assay and by absorbance at 260 nm. The amount of total mRNA from various samples extracted with oligo-(dT) cellulose (MicroFestTrack 228; Invitrogen) was measured by both the GENEPLATE™ (oligonucleotide-immobilized microplate) and $A_{260}$ according to the relation 1.0 $A_{260}$=40 μg of mRNA per milliliter in the GENEPLATE™ (oligonucleotide-immobilized microplate), the amount of mRNA was determined from the calibration curve for rabbit globin mRNA (see FIG. 3). Both values were well correlated with each other (r=0.918, n=10).

EXAMPLE 3: Quantification of Cellular mRNA

Because absolute values of total cellular mRNA are not well characterized, we applied the GENEPLATE™ (oligonucleotide-immobilized microplate) to measurement of mRNA in various cells. We first tested several sample preparation procedures for different cells and tissues. In our initial experiments, whole cells were lysed by SDS and proteinase K to release mRNA from both nuclei and cytoplasm. However, because of strong viscosity (mainly from genomic DNA and proteins), the resulting YOYO-1™ signals were not consistent. Therefore, in the present study, we lysed the cells with mild detergent (50 mL/L NP-40) in the presence of an RNAse inhibitor (20 mmol/L VRC) for 5 min on ice to release cytoplasmic mRNA, and then centrifuged the tubes to pellet the nuclei and other cellular debris. The resulting supernatant solutions were applied to the GENEPLATE™ (oligonucleotide-immobilized microplate) for hybridization. This lysis procedure is rapid, easy to manipulate, and provides consistent results.

When we used this lysis procedure, the amounts of mRNA in $10^6$ undifferentiated U937 and HL-60 cells were 268.6±13.1 μg/mL (n=8) and 282.0±7.8 μg/mL (n=8), respectively. Interestingly, the amount of total mRNA decreased during PMA-induced differentiation in both cell lines; by 48 h after PMA treatment, mRNA contents in $10^6$ differentiated U937 and HL-60 cells were 145.3±13.9 μg/mL (n=8, P<0.01) and 164.7±11.6 μg/mL (n=8, P<0.01), respectively.

Figure 5B:
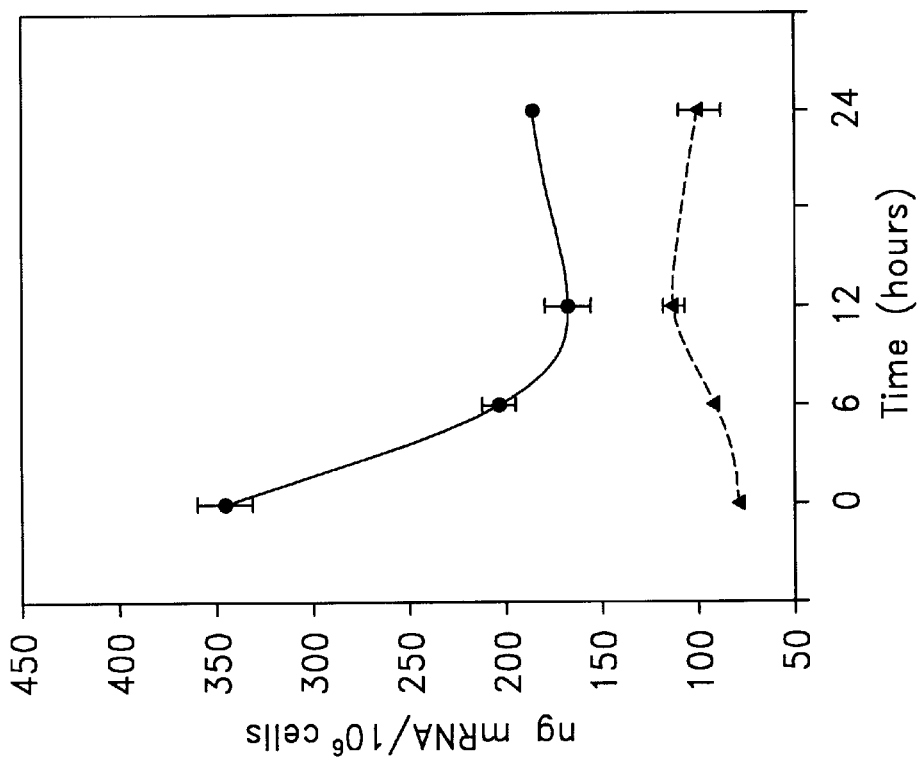
FIG. 5 is a graph showing the relationship between mRNA production and time (hours), i.e., effect of serum deprivation on cytosolic mRNA, in undifferentiated cells or differentiated cells, wherein the U937 cell line is used in FIG. 5A, and the HL-60 cell line is used in FIG. 5B.
Figure 5A:
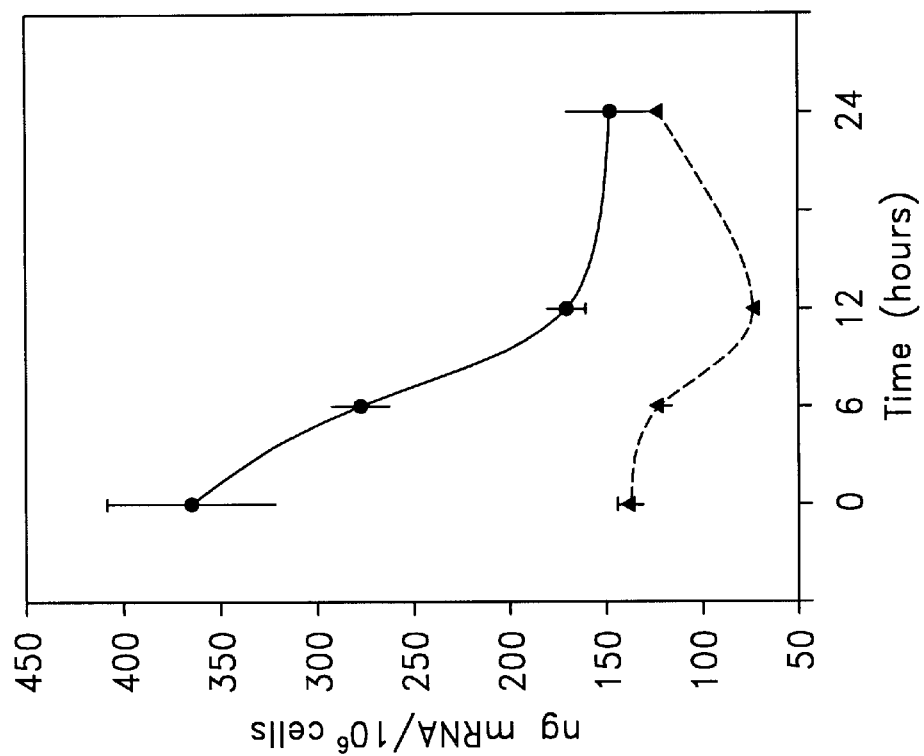

In this Example, the response of mRNA to growth stimuli was more sensitive in undifferentiated cells than in differentiated cells (FIGS. 5 and 6). Furthermore, the amounts of mRNA in undifferentiated cells decreased rapidly by deprivation of serum (FCS), whereas the mRNA content remained stable in differentiated bells. Because mRNA content in undifferentiated adherent CaR-1 colon cancer cells decreased within 6 hours after serum deprivation from 337.9±14.0 ng to 102.6±3.4 ng per $10^6$ cells (n=3) (data not shown), hyperresponsiveness to serum deprivation is likely to be related to the cellular differentiation status, not to the cell's adherent/floating characteristics.

EXAMPLE 4: Response to Serum Deprivation/Stimulation

Although mRNA content was constant when cells were cultured in media containing 100 mL/L FCS, the amount of cellular mRNA in undifferentiated U937 and HL-60 cells decreased within 6–12 h when FCS concentrations were changed from 100 to 5 mL/L in the culture media (FIG. 5). More interestingly, mRNA amounts in both PMA-induced differentiated U937 and HL-60 cells remained unchanged after serum deprivation (FIG. 5).

In contrast to serum deprivation, the amount of mRNA in both undifferentiated U937 and HL-60 cells significantly increased when cells were stimulated with 100 mL/L FCS after serum starvation (5 mL/L FCS) for 24 h (FIG. 6). Peak mRNA amounts were reached approximately 12 hours after serum stimulation in both cell lines, and the amount of mRNA decreased in conjunction with cellular confluency (FIG. 6).

In the above, FIG. 5 shows the effects of serum deprivation on cytosolic mRNA. U937 (A) had HL-60 (B) cells were cultured in RPMI containing appropriate antibiotics and 100 mL/L FCS in the presence of 160 nmol/L PMA for 3 days to induce differentiation. Both undifferentiated (●) and differentiated (▲) cells were resuspended for various periods in fresh RPMI containing 5 mL/L FCS for various periods. Cells were washed with PBS and then resuspended in 200 μL of lysal buffer (50 mmol/L Tris, pH 7.5 1 mmol/L EDTA 0.4 mol/L NaCl) containing 5 mL/L NP-40 and 10 mmol/L VRC for 5 min. on ice. After centrifugation at 15 000 g for 5 min., 50 µL of the supernatant solution was applied to each well of the GENEPLATE™ (oligonucleotide-immobilized microplate) for hybridization; this was followed by mRNA measurement by Yoyo-1™ as described in the text and in FIGS. 3 and 4. All data are expressed as the mean+ SE from two separate determinations, each performed in triplicate. FIG. 6 shows the effects of serum stimulation on cytosolic mRNA. Undifferentiated U937 (A) and HL-60 (B) cells were cultured for 24 h in RPMI containing 5 mL/L FCS, and then for the next 12–96 h were resuspended in fresh RPMI containing 100 mL/L FCS. The number of cells in each well (■) was measured with a hemocytometer, and the amount of cytosolic mRNA (●) was measured by the GenePlate (see text and FIGS. 3–5). all data are expressed as the mean ±SE from three separate determinations, each performed three times.

As explained above, performed was a rapid and nonradioactive method of quantifying cytosolic mRNA from crude cell lysates by using plastic plates to which oligonucleotides containing poly-(dT) sequences were previously immobilized. Captured mRNA on the plate was mixed with YOYO-1™ fluorescent indicator dye, and the resulting YOYO-1™ fluorescence of the mRNA-YOYO-1™ complex was measured in a fluorometer. Because YOYO-1™ signals were linearly increased in proportion to the amount of applied mRNA in the range 10–250 mg, the amount of mRNA in test samples can be determined by comparing their YOYO-2™ fluorescence with that of known concentrations of calibrator mRNA. Using this system, we found that the amount of cytosolic mRNA in undifferentiated U937 and HL-60 cells was 268.6+13.1 and 282.0±7.8 ng/$10^6$ cells, respectively, significantly P <0.01) more than that of phorbol ester-induced differentiated U937 and HL-60 cells (145.3±13.9 and 164.7±11.6), respectively. Therefore, the present system may be applicable to both medical molecular biology research and diagnostics.

<EXAMPLE: CHEMOSENSITIVITY TESTS>
Materials

The U937 human histiocytic lymphomas cell line exhibiting monocyte characteristics, the HL-60 human promyelocytic leukemia cell line, and the HepG2 human hepatocellular line with epithelial morphology (American Type Culture Collection, Rockville, Md.), cell culture media and fetal calf serum (FCS), phosphate buffered saline (PBS), rabbit globin mRNA, vanadyl ribosyl complex (VRC) (Gibco-BRL, Gaithersburg, Mich.), GENEPLATE™ (oligonucleotide-immobilized microplate) (Hitachi Chemical Research Center, Irvine, Calif.) (Mitsuhashi et al., *Nature* 1992; 357:519–520) were from the designated suppliers. The CaR-1 human colon cancer cell line (JCRB0207) was a gift from Dr. K. Miyazaki (Kihara Institute for Biological Research, Yokohama, Japan). YOYO-1™ was purchased from Molecular Probes (Eugene, Oreg.). All other chemicals were purchased from Sigma (St. Louis, Mis.). Oligonucleotides were synthesized by a synthesizer (Applied Biosystems, San Jose, Calif.) according to the manufacturer's protocol.

Cell culture

U937, HL-60 and CaR-1 cells were grown in RPMI 1640 containing 50 units/ml penicillin, 50 µg/ml streptomycin, and 10% FCS at 37° C. in 5% $CO_2$, 95% air. HepG2 cells were grown in Eagle's minimum essential medium (MEM) with 0.1 mM nonessential amino acids, 1 mM sodium pyruvate and Earle's balance solution (BSS). Floating cells were subcultured two to three times a week and adherent cells were removed by trypsinization and subcultured two to four times a month. Initial cell viability was always more than 95% as assessed by the exclusion of trypan blue (Ausubel et al., *Current Protocols in Molecular Biology*, John Wiley & Sons 1988; 11.5.1–11.5.2). The number of cells was determined in a hemocytometer.

Drugs

The following drugs have been tested using the reported peak plasma concentrations (PPCs) achieved during intravenous administration of clinical doses (Werner et al., *Cancer Treat Rep* 1986; 70:1379–1382). Vinblastine 0.5 mg/ml; Cisplatin 2 mg/mi; Mitomycin C 3 mg/ml. The drugs were tested at 0.001, 0.01, 0.1, 1.0 and 10x PPC. Vinblastine was occasionally tested at 100x PPC. These results were used to calculate the concentration of each drug which exhibits 50% inhibition ($IC_{50}$).

MTT assay

Cells were suspended in medium supplemented with 10% FCS, and 100 µl of single cell suspension containing $1 \times 10^5$ cells were added to the individual wells on 96 well microtiter plates. One hundred µl of anticancer drugs were added to each well to give the final concentrations as indicated above. The plates were incubated at 37° C. in a humidified atmosphere containing 5% $CO_2$ in air for various periods. Twenty µl of 0.25% MTT in PBS was added to each well, and plates were incubated for an additional three hours. After centrifugation, supernatant solutions were removed and 200 µl of dimethyl sulfoxide were added to dissolve formazon products, and the plates were shaken for five minutes on a plate shaker (IS-963, Tomy, Palo Alto, Calif.). The absorbance of the well was read on a microplate spectrophotometer (Thermo max, Molecular Device, Mountain View, Calif.) using wavelength at 560 nm.

mRNA assay

Detailed procedures were described in our previous publication (Tominaga et al., *Clin. Chem.* 1996; 42:11, 1750–1757). In brief, 1 ml of cell suspension containing $5 \times 10^5$ cells were plated to each well of 12-well tissue culture plates for various periods, and each drug was exposed continuously or for two hours. Harvested cultured cells were washed with PBS one to two times. Cells were then resuspended in 200 µl of diethylpyrocarbonate (DEPC) -treated lysis buffer (10 mM Tris, pH7.5, 1 mM EDTA, 0.5M NaCl, 0.5% NP-40 and 20 mM VRC for five minutes on ice, then immediately centrifuged at 15,000 xg at 4° C. for five minutes. Fifty µl each of the supernatant was applied to the GENEPLATE™ (oligonucleotide-immobilized microplate) (Mitsuhashi et al., *Nature* 1992, 357:519–520). After one hour incubation at room temperature, unbound non-mRNA was removed by aspiration and washed with a low salt buffer (10 mM Tris, pH 7.6, 1 mM EDTA, 0.1 M naCl) three times. Fifty µl of YOYO-1™ in the final dilution of 1:1000 in TAE buffer (40 mM Tris-acetate, pH 8.0, 1 mM EDTA) was added to each well, and the fluorescence intensity of each well was measured by a fluorescent plate reader (CytoFlour™ 2300, Millipore, Bedford, Mass.) with excitation and emission wavelengths of 485 nm (bandwidth 20 nm) and 530 nm (bandwidth 25 nm), respectively, as previously described (Glazer et al., *Nature* 1992;359:859–861 and Ogura et al., *Biotechniques* 1994; 18:231–232).

EXAMPLE 5: CYTOTOXICITY TEST

Figure 8A:
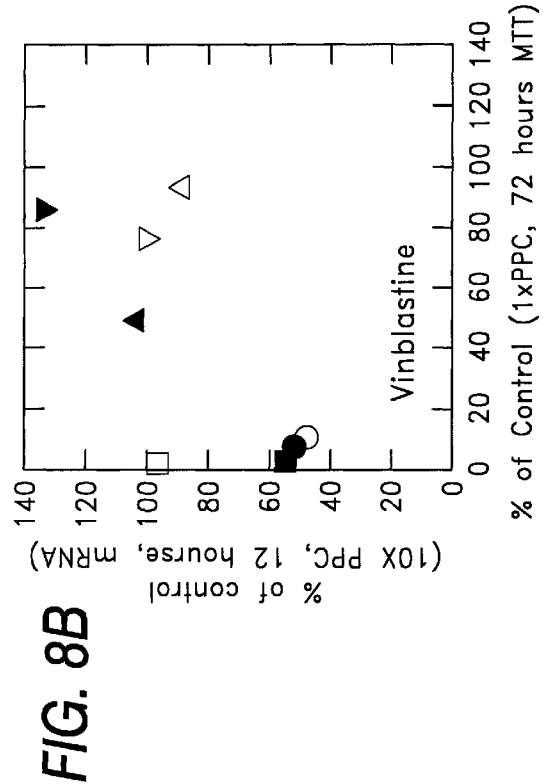
FIG. 8 is a graph showing the relationship between the data (% of control) of three-day MTT assay and that of 12-hour mRNA assay, when incubating U937, HL-60, CaR-1, and HepG2 cell lines with 1× or 10× PPC of cisplatin (FIG. 8A), vinblastine (FIG. 8B), or mitomycin C (FIG. 8C).
FIG. 8D shows total results.
Figure 8B:
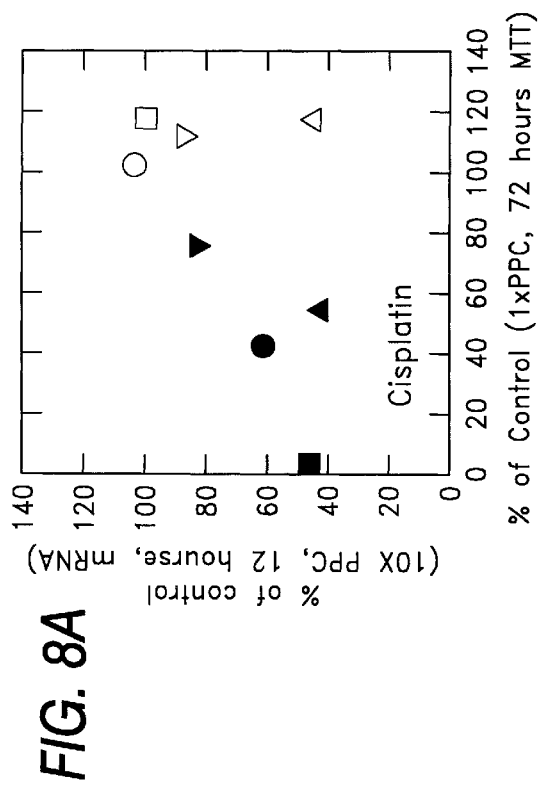
Figure 8C:
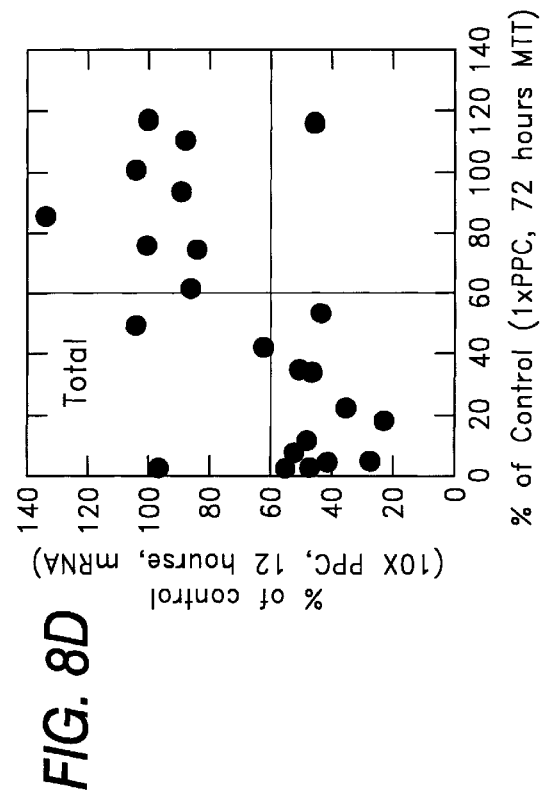

First, we have confirmed cytotoxicity of vinblastine, cisplatin, and mitomycin C on four different cell lines by using conventional MTT assay with standard three days' incubation (Table I). Chemosensitivity was assessed for both continuous drug exposure and transient exposure (two hours). Total cytosolic poly(A)+ mRNA was measured as described in the Methods. As shown in Table I, $IC_{50}$ derived from standard MTT assay was within the same range of that of mRNA assay, with only one exception—the effect of vinblastine against HepG2 cells.

mycin C (FIG. 8C) for two hours (○□△▽) or continuously 12–72 hours (●■▲▼). MTT and mRNA assays were carried out as described in the Methods. The data obtained from the three-day MTT assay with 1× PPC (x-axis) were compared with those of the 12-hour mRNA assay with 10× PPC

TABLE I $IC_{50}$ of continuous (72 hours) or transient (2 hours) incubation of cisplatin, vinblastine, and mitomycin C determined by either MTT or total mRNA measurement. Data were the means + standard deviation (n = 4) in $\mu$ g/ml.

|  | Exposure (hours) | Cisplatin MTT | mRNA | Vinblastine MTT | mRNA | Mitomycin C MTT | mRNA |
|---|---|---|---|---|---|---|---|
| U937 | 72 | 1.77 ± 0.05 | 1.58 ± 0.39 | <0.0005 | <0.0005 | 0.29 ± 0.01 | 0.23 ± 0.03 |
|  | 2 | 22.65 ± 0.03 | 18.52 ± 4.69 | 0.034 ± 0.003 | 0.029 ± 0.001 | 2.46 ± 0.04 | 2.01 ± 0.11 |
| HL60 | 72 | 1.14 ± 0.01 | 1.21 ± 0.06 | <0.0005 | <0.0005 | 0.045 ± 0.01 | 0.22 ± 0.01 |
|  | 2 | 12.68 ± 0.30 | 9.30 ± 0.31 | 0.026 ± 0.001 | 0.031 ± 0.004 | 1.34 ± 0.01 | 2.29 ± 0.06 |
| CaR-1 | 72 | 3.08 ± 0.54 | 3.09 ± 0.34 | 22.17 ± 14.44 | 34.89 ± 4.80 | 2.12 ± 0.08 | 2.00 ± 0.16 |
|  | 2 | 20< | 20< | 50< | 50< | 21.31 ± 1.58 | 21.31 ± 0.95 |
| HepG2 | 82 | 8.86 ± 0.40 | 9.81 ± 0.64 | 32.64 ± 8.46 | 3.45 ± 0.63 | 2.08 ± 0.09 | 1.89 ± 0.06 |
|  | 2 | 20< | 20< | 50< | 34.61 ± 1.75 | 24.20 ± 0.81 | 36.92 ± 3.51 |

EXAMPLE 6: KINETIC CHARACTERISTICS

Figure 7:
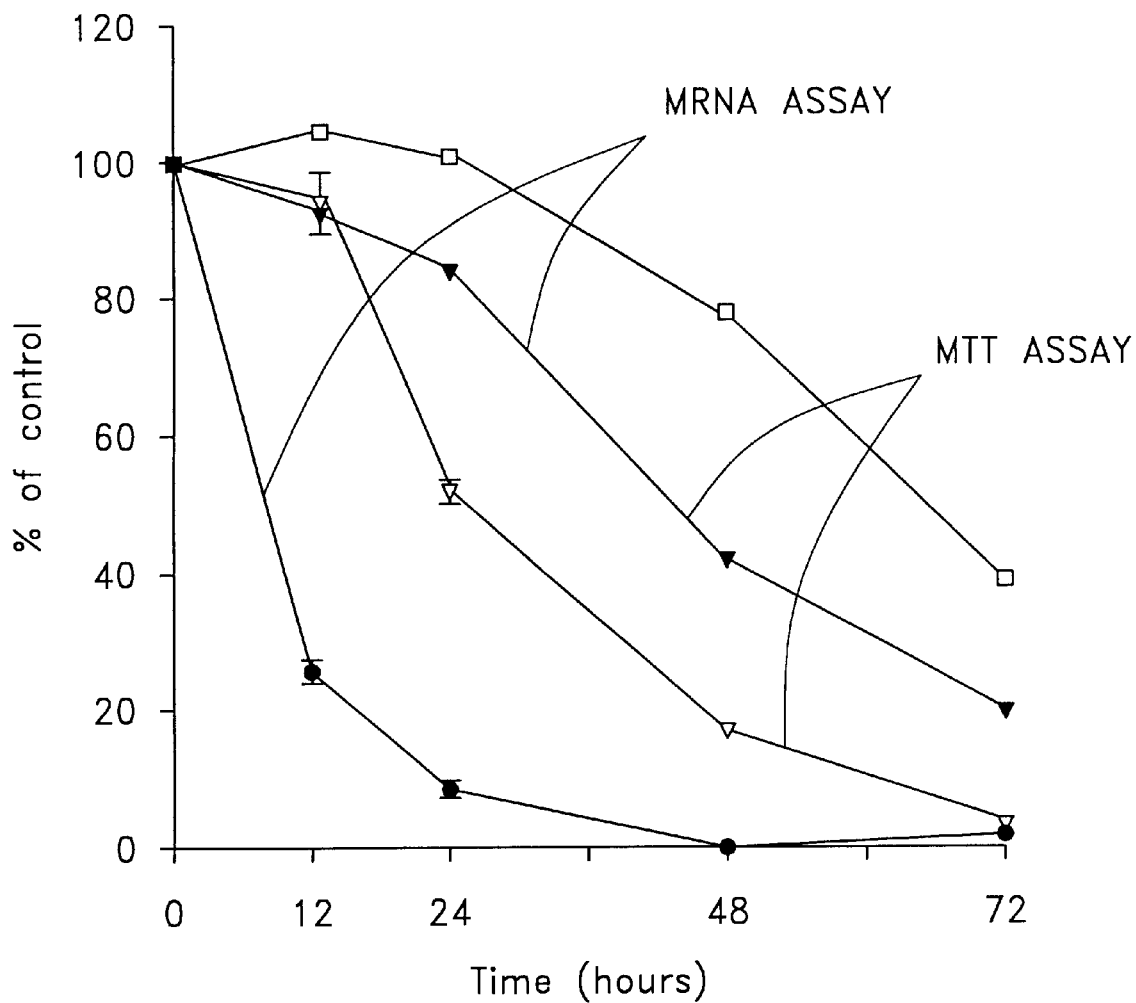
FIG. 7 is a graph showing the relationship between the means±standard error (% of control) and time (hours), i.e., kinetics of cisplatin chemosensitivity, in a mRNA assay or a MTT assay when exposed to 1× PPC or 10× PPC cisplatin.
Figure 8D:
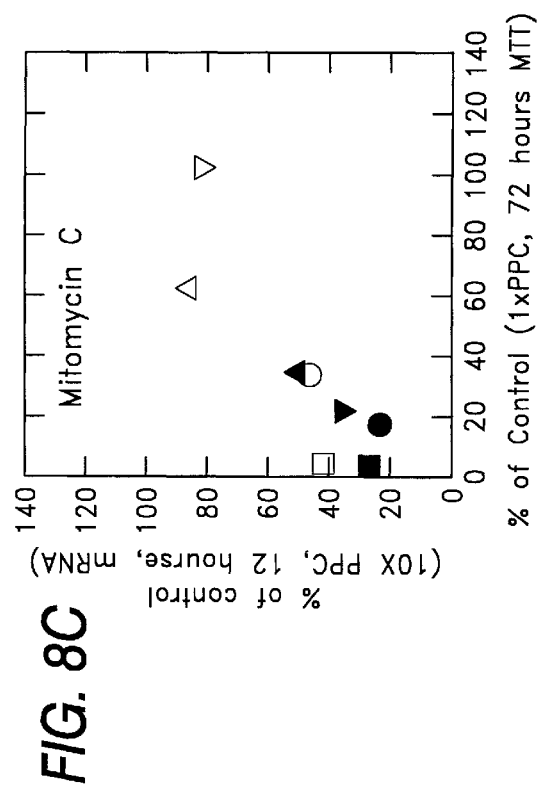
Figure 9A:
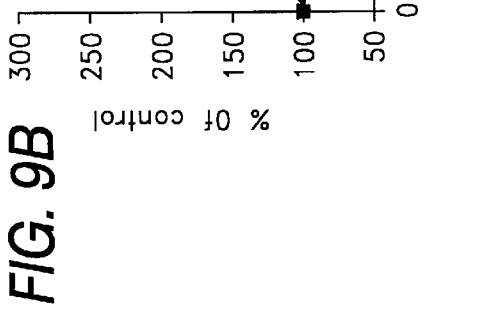
FIG. 9 is a graph showing the relationship between the incubation time in serum-free media and each of cell numbers, cellular viability, MTT assay values, and mRNA assay values, when using U937 (FIG. 9A), HL-60 (FIG. 9B), CaR-1 (FIG. 9C), and HepG2 (FIG. 9D) cell lines.
Figure 9B:
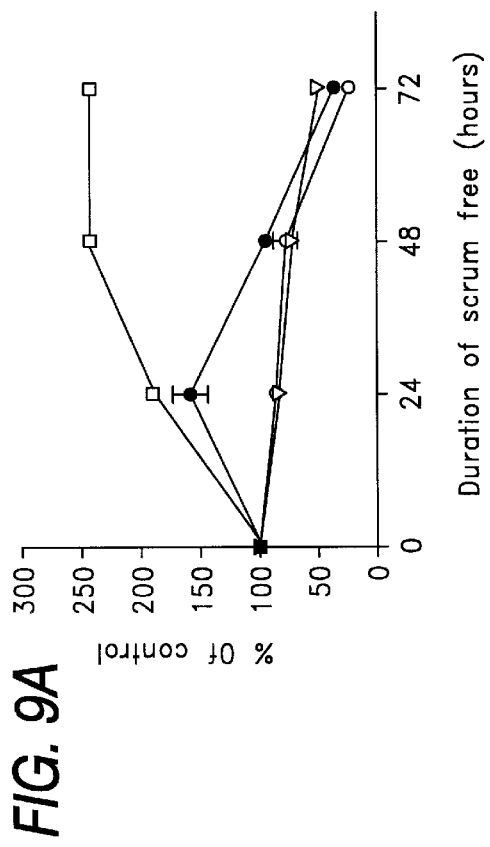
Figure 9C:
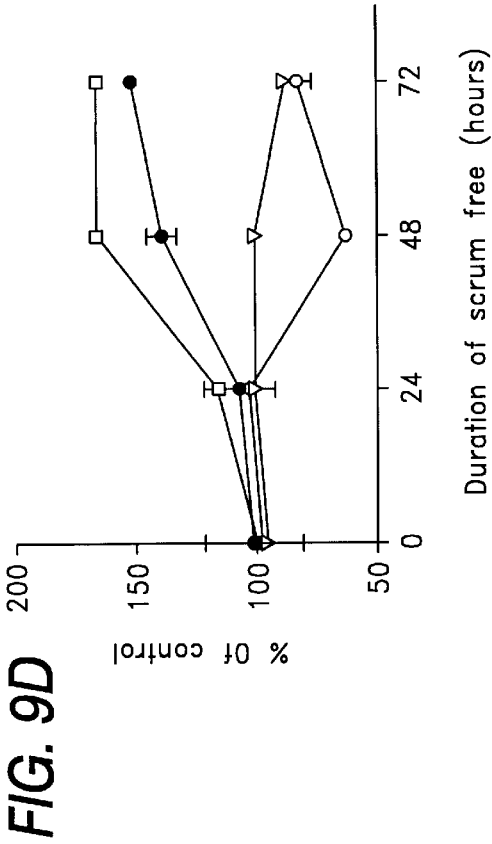
Figure 9D:
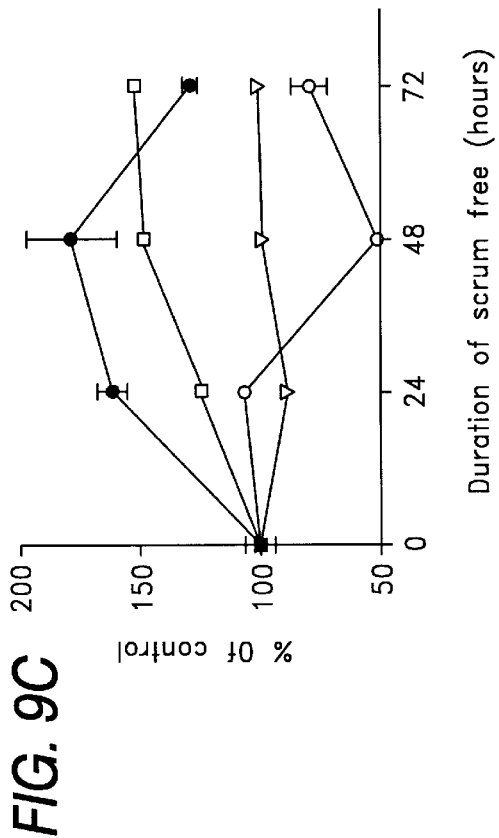

In the kinetic studies as shown in FIG. 7, the cytotoxic effect of cisplatin was detected much earlier in mRNA assay than MTT assay in both 1× and 10× PPC. More interestingly, if 10× PPC is used, the cytotoxic effect of cisplatin was detected as early as 12 hours after drug treatment in mRNA assay, whereas similar reduction of MTT assay was observed 48 hours after drug treatment (FIG. 7). Furthermore, the results of mRNA assay with 10× PPC for 12 hours incubation was significantly correlated with that of the standard three-day MTT assay with 2× PPC with three drugs in four different cell lines (FIG. 8). The emphasis is that sensitive drugs identified by standard three-day MTT assay (% control less than 60%) were also detected by the 12-hour mRNA assay (FIG. 8D, lower left quadrant), whereas drug resistance determined by the MTT assay (% control more than 60%) was also detected by the mRNA assay (FIG. 8D, upper right quadrant), although some exceptions exist (FIG. 8D, lower right and upper left quadrants). Interestingly, these discrepancies (Vinblastine for HL-60 and CaR-1 and Cisplatine for CaR-1 cells) were not the case when $IC_{50}$ was compared (Table I). Therefore, instead of using fixed 10× PPC, as shown in the present study, optimal doses for the 12-hour mRNA assay would be determined for each drug and each cancer cells by using much large clinical isolates.

In the above, FIG. 7 shows kinetics of cisplatin chemosensitivity. U937 cells were seeded at a density of $1 \times 10^6$ cells/ml in RPMI containing 10% FCS in a 96-well plate for MTT assay (▽,□) and a 24-well plate for the mRNA assay (●,▼). Cells were continuously exposed to 1× PPC (2 $\mu$g/ml) (▼,□) or 10× PPC (●,▽) cisplatin for 12 hours to three days, then MTT or mRNA assays were carried out as described in the Methods. The values indicated in the means±standard error of triplicate determinations from a single experiment. Similar results were reproduced in more than three independent experiments (data not shown). FIG. 8 shows the correlation between three-day MTT assay and 12-hour mRNA assay. U937 (●○), HL-60 (■□), CaR-1 (▲△), and HepG2 (▼▽) cells were incubated with 1× or 10× PPC of cisplatin (FIG. 8A), vinblastine (FIG. 8B), or mito- (y-axis). FIG. 8D (Total) is a mixture of FIGS. 8A–8C. Each point represents the means of triplicate determinations.

EXAMPLE 7: CYTOSTATIC CONDITION

In order to analyze minor discrepancies between the MTT and the mRNA assay found in both Table I and FIG. 8, cells were incubated in the absence of FCS for one to three days to analyze cytostatic effects. As shown in FIG. 9, cell numbers increased for the subsequent one to two days even in serum-free media, and became stable after two to three days. Cellular viability was always more than 60%, and once FCS was added after the three-day serum starvation, cell numbers increased significantly (data not shown), suggesting cells were still alive. Interestingly, the results of the MTT assay also increased during the first one to two days in serum-free media, whereas total mRNA content did not increased in all four cells (FIG. 9). Furthermore, the amount of total mRNA per cell significantly decreased because of the increase in cell number in each well (FIG. 9). These data suggest that the changes in total mRNA was responsive for not only cell death, but also cytostatic conditions, whereas MTT assay is more sensitive to cell death.

In the above, FIG. 9 shows MTT and mRNA assays during cytostatic states. U937 (A), HL-60 (B), CaR-1 (C), and HepG2 (D) cells were incubated with serum-free media for one to three days, then cell number (□) and cellular viability (▽) were determined, and the MTT assay (●), and the mRNA assay (○) were carried out as described in the Methods. The results were expressed as % of control based on the date of day 0. All data indicated in the mean±standard error of triplicate determinations from a single experiment. Similar results were reproduced in at least two independent experiments (data not shown).

As explained above, chemosensitivity of vinblastine, cisplatin, and mitomycin C was assessed in four different human cancer cell lines (U937, HL-60, CaR-1, and HepG2) by the MTT (3-(4,5-dimethylthiazol-2-yl)-2.5-diphenyltetrazolium bromide) assay and the measurement of total cytosolic poly(A)+ mRNA. Results of the 12-hour mRNA assay with 10% peak plasma concentration (PPC) were significantly correlated with that of the standard three-day MTT assay with 1× PPC. Furthermore, the mRNA assay was changed more significantly than the MTT assay under cytostatic conditions. Because of its minimum culture requirement (12 hours) and broad spectrum (cytocidal and cytostatic), the mRNA assay will become a useful tool for chemosensitivity test.

It will be understood by those of skill in the art that numerous variations and modifications can be made without departing from the spirit of the present invention. Therefore, it should be clearly understood that the forms of the present invention are illustrative only and are not intended to limit the scope of the present invention.

We claim:

1. A method for quantifying total mRNA in a biological sample containing mRNA and other RNAs, comprising the steps of:
   (a) incubating said sample with a microtiter plate to which oligonucleotides having oligo-(dT) sequences are immobilized covalently, in the presence of a hybridization buffer to hybridize mRNA present in said sample with said oligonucleotides at said oligo-(dT) sequences, said hybridization buffer including an RNAse inhibitor when RNAse is active in the sample;
   (b) washing non-hybridized components from said microtiter plate;
   (c) contacting components hybridized with said immobilized oligonucleotides with a fluorescent nucleic-acid dye which undergoes excitation when being bound to nucleic acid;
   (d) measuring the intensity of fluorescence which is emitted from said microtiter plate, excluding the background fluorescence of the microtiter plate;
   (e) correlating the measured intensity of fluorescence with the quantity of total mRNA excluding other RNAs present in said sample wherein the other RNAs are excluded in step (b); and
   (f) quantifying the total mRNA from the correlated intensity of fluorescence without contamination of other RNAs.

2. A method for quantifying total mRNA according to claim 1, wherein step (d) comprises the steps of:
   (i) heat-denaturing said mRNA labeled in step (c);
   (ii) washing said denatured mRNA from said microtiter plate; and
   (iii) measuring the amount of label remaining on said microtiter plate;
   wherein, in step (e), the amount of the measured label is the amount of the captured label in step (d) minus the amount of the remaining label in step (iii).

3. A method for quantifying total mRNA according to claim 1, wherein said sample is unpurified cell lysate containing cytosolic mRNA.

4. A method for quantifying total mRNA according to claim 1, wherein said nucleotide sequences are oligo-(dT) sequences.

5. A method for quantifying total mRNA according to claim 1, wherein the length of said nucleotide sequences of said oligonucleotides is at least 15 bases.

6. A method for quantifying total mRNA according to claim 1, wherein, in step (a), RNase inhibitor VRC (vanadyl-ribonucleoside complex) is added to said sample.

7. A method for determining cytotoxic effect of a compound, comprising the steps of:
   (a) adding said compound to sample cells to allow said compound to act on said sample cells for a predetermined period of time, wherein the quantity of total mRNA initially present in said sample cells has been determined;
   (b) measuring the quantity of total mRNA present in said sample cells by a method comprising the steps of:
      (i) incubating a cell lysate of said sample cells with a microtiter plate to which oligonucleotides having oligo-(dT) sequences are immobilized covalently, in the presence of a hybridization buffer to hybridize mRNA present in said sample cells with said oligonucleotides at said oligo-(dT) sequences, said cell lysate including cytosolic mRNA and other RNAs, said hybridization buffer including an RNAse inhibitor when RNAse is active in the sample cells;
      (ii) washing non-hybridized components from said microtiter plate;
      (iii) contacting components hybridized with said immobilized oligonucleotides with a fluorescent nucleic-acid dye which undergoes excitation when being bound to nucleic acid;
      (iv) measuring the intensity of fluorescence which is emitted from said microtiter plate, excluding the background fluorescence of the microtiter plate;
      (v) correlating the measured intensity of fluorescence with the quantity of total mRNA excluding other RNAs present in said sample cells, wherein the other RNAs are excluded in step (ii); and
      (vi) quantifying the total mRNA from the correlated intensity of fluorescence without contamination of other RNAs; and
   (c) evaluating the cytotoxic effect of said compound based on the determined quantity of total mRNA by referring to the initial quantity of total mRNA present in the sample cells.

8. A method for determining cytotoxic effect of a compound according to claim 7, wherein step (iv) comprises the steps of:
   (1) heat-denaturing said mRNA labeled in step (iii);
   (2) washing said denatured mRNA from said microtiter plate; and
   (3) measuring the amount of label remaining on said microtiter plate;
   wherein, in step (v), the amount of the measured label is the amount of the captured label in step (ii) minus the amount of the remaining label in step (3).

9. A method for determining cytotoxic effect of a compound according to claim 7, wherein said compound is an anticancer drug.

10. A method for determining the ratio of the quantity of a particular mRNA having a specific nucleotide sequence, to the quantity of total mRNA in a biological sample containing mRNA and other RNAs, comprising the steps of:
    (a) measuring the quantity of said particular mRNA;
    (b) measuring the quantity of total mRNA present in said sample by a method comprising the steps of:
       (i) incubating said sample with a microtiter plate to which oligonucleotides having oligo-(dT) sequences are immobilized covalently, to hybridize mRNA with said oligonucleotides to said oligo-(dT) sequences;
       (i) incubating said sample with a microtiter plate to which oligonucleotides having oligo-(dT) sequences are immobilized covalently, in the presence of a hybridization buffer to hybridize mRNA present with said oligonucleotides at said oligo-(dT) sequences, said hybridization buffer including an RNAse inhibitor when RNAse is active in the sample;
       (ii) washing non-hybridized components from said microtiter plate;
       (iii) contacting components hybridized with said immobilized oligonucleotides with a fluorescent nucleic-acid dye which undergoes excitation when being bound to nucleic acid;

(iv) measuring the intensity of fluorescence which is emitted from said microtiter plate, excluding the background fluorescence of the microtiter plate;

(v) correlating the measured intensity of fluorescence with the quantity of total mRNA excluding other RNAs present in said sample, wherein the other RNAs are excluded in step (ii); and (vi) quantifying the total mRNA from the correlated intensity of fluorescence without contamination of other RNAs; and (c) correlating the quantity of said particular mRNA with the quantity of the total mRNA.

11. A method for determining the quantity of a particular mRNA according to claim 10, wherein step (iv) comprises the steps of:

(1) heat-denaturing said mRNA labeled in step (iii);

(2) washing said denatured mRNA from said microtiter plate; and (3) measuring the amount of label remaining on said microtiter plate;

wherein, in step (v), the amount of the measured label is the amount of the captured label in step (ii) minus the amount of the remaining label in step (3).

12. A method for quantifying total mRNA according to claim 1, wherein said dye is a fluorescent dye selected from the group consisting of 1,1'-(4,4,7,7-tetramethyl4,7-diazaundecamethylene)-bis4-(3-methyl-2,3-dihydro-(benzo-1,3-oxazole)-2-methylidene)-quinoliumetraiodide YOYO-1),1,1'-(4,4,7,7-tetramethyl-4,7-diazaundecamethylene)-bis-4-(3-methyl-2,3-dihydro-(benzo-1,3-thiazole)-2-methylidene)-quinoliumetraiodide (TOTO-1), and 1,1'-(4,4,7,7-tetramethyl-4,7-diazaundecamethylene)-bis-4-(3-methyl-2,3-dihydro-(benzo-1,3-thiazole)-2-propenylidene)-quinoliumetraiodide (TOTO-3).

* * * * *

UNITED STATES PATENT AND TRADEMARK OFFICE
CERTIFICATE OF CORRECTION

PATENT NO.    : 5,976,767
DATED         : Nov. 2, 1999
INVENTOR(S)   : Li Li

It is certified that error appears in the above-identified patent and that said Letters Patent is hereby corrected as shown below:

Cover Page, References Cited, line 8, change "5,839,198" to --5,839,198--

Cover Page, Abstract, right column, line 16, after "the" delete "of"

Col. 1, line 64, after "a" delete "is"

Col. 4, line 31, after "10" insert --is--

Col. 5, line 8, after "consisting" insert --of--

Col. 5, line 36, after "consisting" insert --of--

Signed and Sealed this

Twenty-seventh Day of March, 2001

*Attest:*

NICHOLAS P. GODICI

*Attesting Officer*     Acting Director of the United States Patent and Trademark Office